US010925890B2

(12) United States Patent
Waas et al.

(10) Patent No.: US 10,925,890 B2
(45) Date of Patent: Feb. 23, 2021

(54) USE OF DEXTRAN SULFATE

(71) Applicant: TX MEDIC AB, Viken (SE)

(72) Inventors: Anders Waas, Gothenburg (SE); Lars Bruce, Viken (SE); Adam Bruce, Viken (SE)

(73) Assignee: TX MEDIC AB, Viken (SE)

( * ) Notice: Subject to any disclaimer, the term of this patent is extended or adjusted under 35 U.S.C. 154(b) by 0 days.

(21) Appl. No.: 16/545,666

(22) Filed: Aug. 20, 2019

(65) Prior Publication Data

US 2019/0381090 A1 Dec. 19, 2019

Related U.S. Application Data

(63) Continuation of application No. 15/316,789, filed as application No. PCT/SE2015/050677 on Jun. 11, 2015, now Pat. No. 10,485,817.

(30) Foreign Application Priority Data

| Jun. 12, 2014 | (SE) | 1450729-7 |
| Sep. 22, 2014 | (SE) | 1451120-8 |
| Dec. 15, 2014 | (SE) | 1451540-7 |

(51) Int. Cl.
*A61K 31/721* (2006.01)
*A61K 9/00* (2006.01)
*A61K 9/08* (2006.01)

(52) U.S. Cl.
CPC .......... *A61K 31/721* (2013.01); *A61K 9/0019* (2013.01); *A61K 9/08* (2013.01)

(58) Field of Classification Search
None
See application file for complete search history.

(56) References Cited

U.S. PATENT DOCUMENTS

| 5,135,920 | A | 8/1992 | Kanamaru et al. |
| 5,605,891 | A | 2/1997 | Prino et al. |
| 5,744,155 | A | 4/1998 | Friedman et al. |
| 6,106,554 | A | 8/2000 | Bretton |
| 6,440,947 | B1 | 8/2002 | Barron et al. |
| 2003/0171287 | A1 | 9/2003 | Morishita et al. |
| 2009/0081125 | A1 | 3/2009 | Shindo |
| 2010/0087393 | A1 | 4/2010 | Bansal |
| 2010/0113389 | A1 | 5/2010 | Nilsson et al. |
| 2010/0240735 | A1 | 9/2010 | Morishita et al. |
| 2012/0110683 | A1 | 5/2012 | Shomura et al. |

FOREIGN PATENT DOCUMENTS

| AU | 595382 B2 | 3/1990 |
| JP | 53-96128 A | 4/1988 |
| JP | 2-223525 A | 9/1990 |
| JP | 6-157322 A | 6/1994 |
| JP | 2005104910 A | 4/2005 |
| JP | 2012025759 A | 2/2012 |
| KR | 10-0798566 B1 | 1/2008 |
| WO | 2004/047848 A1 | 6/2004 |
| WO | 2006/134692 A1 | 12/2006 |

OTHER PUBLICATIONS

Ukita, Minoru et al., Observations on anticoagulant activity of dextran sulfate (MDS), Blood & Vessel, vol. 12, pp. 127-129 (1981), including English abstract.
Iijima, Kenji et al., Inhibitory effects of DS and heparin on the fibrinogen-fibrin conversion, Blood & Vessel, vol. 13, pp. 585-588 (1982), including English abstract.
Official Action dated Mar. 5, 2019 from corresponding Japanese Application No. 2016-572597 and English machine translation.
Gajanayake, T. et al., Dextran Sulfate Facilitates Anti-CD4 mAb-Induced Long-Term Rat Cardiac Allograft Survival After Prolonged Cold Ischemia, American Journal of Transplantation, 8:1151-1162 (2008).
Strilic, Boris et al., Electrostatic Cell-Surface Repulsion Initiates Lumen Formation in Developing Blood Vessels, Current Biology, 20:2003-2009 (2010).
Jackson, Christopher J. et al., Sulfacted Polysaccharides Are Required for Collagen-Induced Vascular Tube Formation, Experimental Cell Research, 215:294-302 (1994).
Hiebert, Linda M. et al., Dextran Suphates Protect Porcine Arterial Endothelial Cells from Free Radical Injury, Human & Experimental Toxicology, vol. 13, pp. 233-239 (1994).
Official Action dated Dec. 17, 2018 from corresponding Korean Application No. 10-2017-7000785, with English Translation.
Banz, Yara et al., Locally targeted cytoprotection with dextran sulfate attenuates experimental procine myocardial schaemia/reperfusion injury, European Heart Journal, vol. 26, pp. 2334-2342 (2005).
Official Action dated Nov. 20, 2018 from corresponding to Japanese Patent Application No. 2016-572597, and English Translation thereof.
Sigma-Aldrich, website capture of http://www.sigmaaldrich.com, retrieved on Apr. 26, 2018 (2014).
Falconer, D. J. et al., Biosynthesis of dextrans with different molecular weights by selecting the concentration of Leuconostoc mesenteroides B-512FMC dextransucrase, the sucrose concentration, and the temperature, Carbohydrate Research, vol. 346, No. 2, pp. 280-284 (2011).
Izunobi, J. U. et al., Polymer molecular weight analysis by 1H NMR spectroscopy, Journal of Chemical Education, vol. 88, No. 8, pp. 1098-1104 (2011).

(Continued)

*Primary Examiner* — Dale R Miller
(74) *Attorney, Agent, or Firm* — Porter Wright Morris & Arthur LLP

(57) ABSTRACT

The present embodiments relate to the use of dextran sulfate having an average molecular weight below 10 000 Da for inducing angiogenesis in a subject and for increasing blood flow in a subject suffering from ischemia.

16 Claims, 25 Drawing Sheets

(56) References Cited

OTHER PUBLICATIONS

Hahnenberger, Rudolph et al., Low-sulphated oligiosaccharides derived from heparan sulphate inhibit normal angiogenesis, Glycobiology, vol. 3, No. 6, pp. 567-573 (1993).
Norrby, Klas, Heparin and Angiogenesis: A Low-Molecular-Weight Fraction Inhibits and a High-Molecular-Weight Fraction Stimulates Angiogenesis Systemically, Haemostasis, 23 (suppl 1), pp. 141-149 (1993).

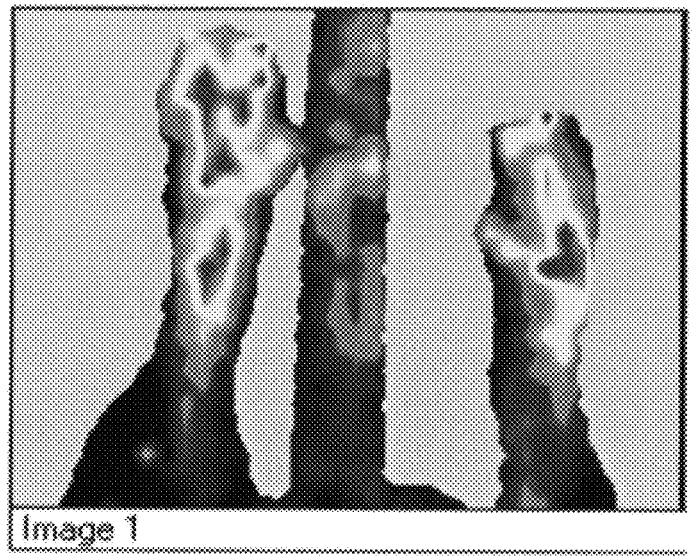
Treatment vs control
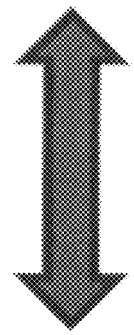
Fig. 8
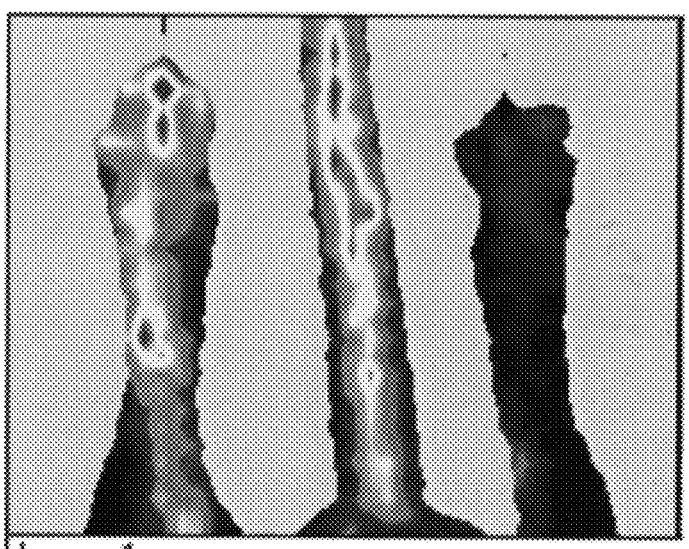

USE OF DEXTRAN SULFATE

CROSS-REFERENCE TO RELATED APPLICATIONS

This application is a continuation application of U.S. patent application Ser. No. 15/316,789, filed Dec. 6, 2016, which is a 371 of PCT/SE2015/050677, filed Jun. 11, 2015.

TECHNICAL FIELD

The present embodiments generally relate to angiogenesis, and in particular to the use of dextran sulfate for inducing angiogenesis in a subject.

BACKGROUND

Angiogenesis is the physiological process through which new blood vessels form from pre-existing vessels. This is distinct from vasculogenesis, which is the de novo formation of endothelial cells from mesoderm cell precursors. The first vessels in the developing embryo form through vasculogenesis, after which angiogenesis is responsible for most, if not all, blood vessel growth during development and in disease.

Angiogenesis is a normal and vital process in growth and development, as well as in wound healing and in the formation of granulation tissue.

Angiogenesis is traditionally classified as either sprouting angiogenesis or intussusception, or splitting angiogenesis. Sprouting angiogenesis forms entirely new blood vessels, whereas splitting angiogenesis split an existing blood vessel into two.

Angiogenesis may be a target for combating diseases characterized by either poor vascularization or abnormal vasculature. The absence of blood vessels in a repairing or otherwise metabolically active tissue may inhibit repair or other essential functions. Several diseases, such as ischemic chronic wounds, are the result of failure or insufficient blood vessel formation and may be treated by a local expansion of blood vessels, thus bringing new nutrients to the site, facilitating repair.

The modern clinical application of the principle of angiogenesis can be divided into two main areas: anti-angiogenic therapies and pro-angiogenic therapies. Whereas anti-angiogenic therapies are being employed to treat or prevent cancer and malignancies, which require an abundance of oxygen and nutrients to proliferate, pro-angiogenic therapies are being explored as options to treat, for instance, cardiovascular diseases, coronary artery disease, atherosclerotic diseases, coronary heart disease, peripheral arterial disease, wound healing disorders, etc.

Traditional approaches in pro-angiogenic treatment include, among others, gene therapy, targeting genes of interest for amplification or inhibition; protein therapy, which primarily manipulates angiogenic growth factors; and cell based therapies, which involve the implantation of specific cell types.

There are still serious, unsolved problems related to gene therapy. Difficulties include effective integration of the therapeutic genes into the genome of target cells, reducing the risk of an undesired immune response, potential toxicity, immunogenicity, inflammatory responses, and oncogenesis related to the viral vectors used in implanting genes and the sheer complexity of the genetic basis of angiogenesis.

Pro-angiogenic protein therapy uses various growth factors, such as fibroblast growth factor (FGF) and vascular endothelial growth factor (VEGF), to promote angiogenesis. An obstacle of protein therapy is the mode of delivery. Oral, intravenous, intra-arterial, or intramuscular routes of protein administration are not always as effective, as the therapeutic protein may be metabolized or cleared before it can enter the target tissue. Cell based pro-angiogenic therapies are still in early stages of research, with many open questions regarding best cell types and dosages to use.

Ischemia is a restriction in blood supply to tissues, causing a shortage of oxygen and glucose needed for cellular metabolism. Ischemia is generally caused by problems with blood vessels, with resultant damage to or dysfunction of tissue. It also means local anemia and hypoxia in a given part of a body sometimes resulting from congestion, such as vasoconstriction, thrombosis or embolism.

Restoration of coronary blood flow after a period of prolonged ischemia often involve so-called reperfusion injury causing endothelial damage and an affected endothelium that takes on pro-coagulant and pro-inflammatory phenotype. The reperfusion greatly accelerates ischemia-induced complement activation and deposition.

Dextran sulfate is a well-known complement inhibitor and has therefore been proposed to achieve cytoprotection of endothelium against reperfusion injury following ischemia.

*Experimental Cell Research* 215, 294-302 (1994) discloses that sulfated polysaccharides, such as heparin and dextran sulfate, can be used in vitro for collagen-induced vascular tube formation. However, in vivo experimental data indicated that the low molecular weight sulfated polysaccharide heparin (2.4 kDa) inhibited angiogenesis, *Glycobiology* 3, 567-573 (1993), *Pathophysiology of Haemostasis and Thrombosis* 23, 141-149 (1993).

U.S. Pat. No. 5,135,920 discloses that dextran sulfate with an average molecular weight of 500 000 Da is angiostatic, i.e. inhibits angiogenesis.

There is still room for improvements within the field of angiogenesis in the art.

SUMMARY

It is a general objective to induce angiogenesis in a subject.

It is another objective to increase blood flow in a subject suffering from ischemia.

These and other objectives are met by embodiments as disclosed herein.

An aspect of the embodiments relates to dextran sulfate, or a pharmaceutically acceptable derivative thereof, having an average molecular weight below 10 000 Da for inducing angiogenesis in a subject.

Another aspect of the embodiments relates to a method for inducing angiogenesis in a subject. The method comprises administering dextran sulfate, or a pharmaceutically acceptable derivative thereof, having an average molecular weight below 10 000 Da to the subject.

A further aspect of the embodiments relates to use of dextran sulfate, or a pharmaceutically acceptable derivative thereof, having an average molecular weight below 10 000 Da for the manufacture of a medicament for inducing angiogenesis in a subject.

Yet another aspect of the embodiments relates to dextran sulfate, or a pharmaceutically acceptable derivative thereof, having an average molecular weight below 10 000 Da for increasing blood flow in a subject suffering from ischemia.

A further aspect of the embodiments relates to a method for increasing blood flow in a subject suffering from ischemia. The method comprises administering dextran sulfate, or a pharmaceutically acceptable derivative thereof, having an average molecular weight below 10 000 Da to said subject.

Still another aspect of the embodiments relates to use of dextran sulfate, or a pharmaceutically acceptable derivative thereof, having an average molecular weight below 10 000 Da for the manufacture of a medicament for increasing blood flow in a subject suffering from ischemia.

Yet another aspect of the embodiments relates to dextran sulfate, or a pharmaceutically acceptable derivative thereof, having an average molecular weight below 10 000 Da for vascularizing ischemic tissue in a subject.

A further aspect of the embodiments relates to a method for vascularizing ischemic tissue in a subject. The method comprises administering dextran sulfate, or a pharmaceutically acceptable derivative thereof, having an average molecular weight below 10 000 Da to said subject.

Still another aspect of the embodiments relates to use of dextran sulfate, or a pharmaceutically acceptable derivative thereof, having an average molecular weight below 10 000 Da for the manufacture of a medicament for vascularizing ischemic tissue in a subject.

Further aspect of the embodiments relates to dextran sulfate, or a pharmaceutically acceptable derivative thereof, having an average molecular weight equal to or below 10 000 Da for in vitro or ex vivo use in inducing angiogenesis in an organ and/or vascularized tissue, for in vitro or ex vivo use in increasing blood flow in a vascularized tissue and/or organ and/or for in vitro or ex vivo vascularizing a vascularized tissue and/or organ, and related methods therefor.

BRIEF DESCRIPTION OF THE DRAWINGS

The embodiments, together with further objects and advantages thereof, may best be understood by making reference to the following description taken together with the accompanying drawings, in which:

FIG. 5B—mouse from group 3M dextran sulfate 30 mg/kg repeated; FIG. 5C—mouse from group 4M dextran sulfate 30 mg/kg single). The left diagrams illustrate CD34 staining and the right diagrams illustrate FITC-labeled dextran staining.

FIG. 8 compares blood flow measured in two mice with non-contact laser Doppler images 35 days after femoral artery ligation of the left hind limb. The lower panel has been vehicle treated (group 1M), the top panel has received treatment with dextran sulfate (group 3M).

Figure 1:
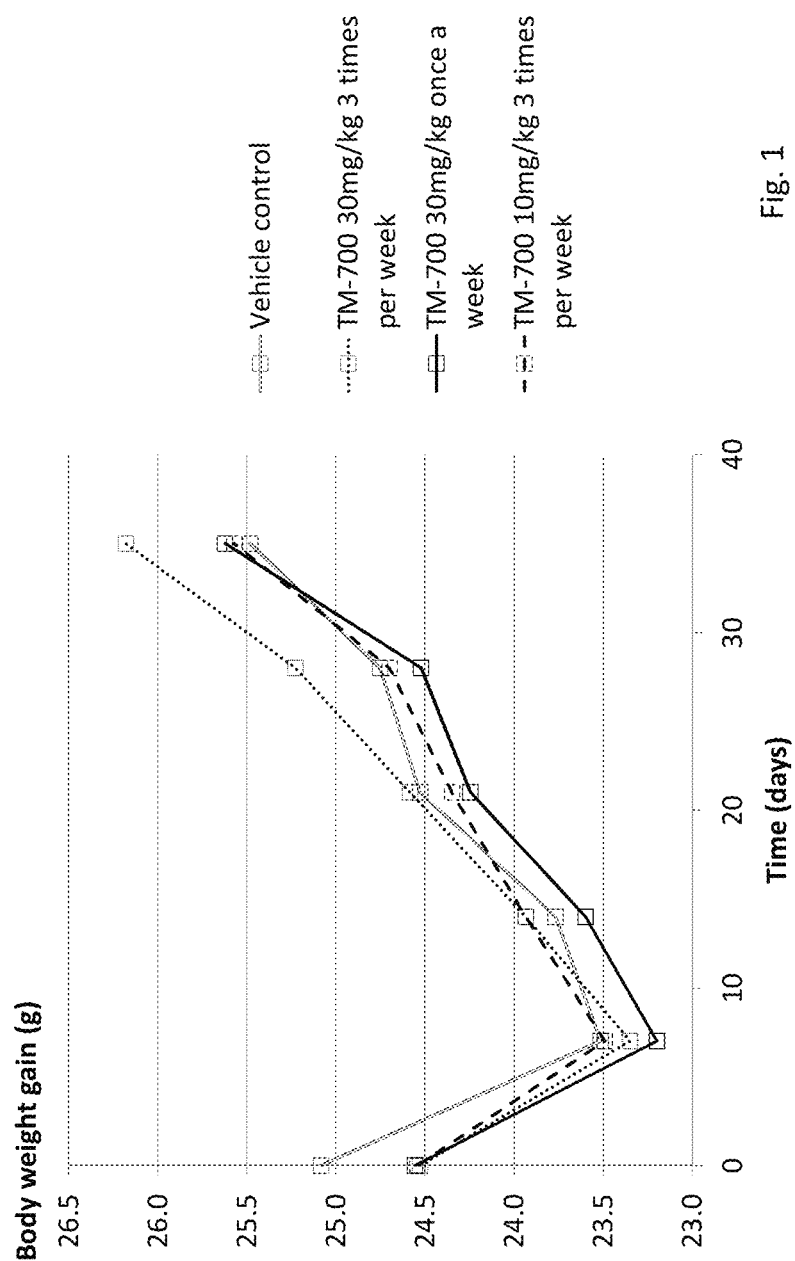
FIG. 1 is a diagram illustrating mean body weight throughout the mouse critical limb ischemia model. Two-way ANOVA followed by Bonferroni post-hoc comparisons revealed no statistically significant differences between the groups.

All figures shows average+standard error of the mean

DETAILED DESCRIPTION

The present embodiments generally relate to angiogenesis, and in particular to the use of dextran sulfate for inducing angiogenesis in a subject.

The present embodiments are based on the discovery that dextran sulfate within a particular average molecular weight has angiogenesis inducing effect and blood flow increasing effect when administered to a subject, preferably a mammalian subject, and more preferably a human subject.

This effect of dextran sulfate of the embodiments was highly surprising in the light of the prior art disclosing that sulfated polysaccharides inhibited angiogenesis in vivo and that dextran sulfate with an average molecular weight of 500 000 Da is angiostatic, i.e. inhibits angiogenesis.

Experimental data as presented in herein in clear contrast shows that dextran sulfate of the embodiments has in vivo effects in inducing angiogenesis as seen by significantly increasing mean blood flow, decreasing ischemia severity, increasing capillary density in an ischemia model and in a stroke model and reducing infarct size in a myocardial infarction (MI) model. The dextran sulfate of the embodiments is furthermore capable of selectively forming blood vessels in ischemic tissue, while not causing any significant vessel formation in non-ischemic tissue.

Accordingly, an aspect of the embodiments relates to dextran sulfate, or a pharmaceutically acceptable derivative thereof, having an average molecular weight below 10 000 for use in inducing angiogenesis in a subject.

In the following, reference to (average) molecular weight and sulfur content of dextran sulfate applies also to any pharmaceutically acceptable derivative of dextran sulfate. Hence, the pharmaceutically acceptable derivative of dextran sulfate preferably has the average molecular weight and sulfur content as discussed in the following embodiments.

Dextran sulfate outside of the range of the embodiments are believed to have inferior or indeed no angiogenesis effect at all. For instance, heparin, another sulfated polysaccharide, with an average molecular weight of 2.4 kDa actually inhibited angiogenesis as did larger dextran sulfate molecules (*Pathophysiology of Haemostasis and Thrombosis* 23, 141-149 (1993); U.S. Pat. No. 5,135,920).

Furthermore, dextran sulfate of a molecular weight exceeding 10 000 Da generally has a lower effect vs. side effect profile as compared to dextran sulfate having a lower average molecular weight. This means that the maximum dose of dextran sulfate that can be safely administered to a subject is lower for larger dextran sulfate molecules (>10 000 Da) as compared to dextran sulfate molecules having an average molecular weight within the present range. As a consequence, such larger dextran sulfate molecules are less appropriate in clinical uses when the dextran sulfate is to be administered to subjects in vivo. In addition, large dextran sulfate molecules have in fact the opposite effect as compared to dextran sulfate of the embodiments as is evidenced from U.S. Pat. No. 5,135,920.

Thus, there seems to be a very narrow range with regard to the average molecular weight of dextran sulfate within which dextran sulfate has angiogenesis effect when administered to a subject and that dextran sulfate molecules outside of the range of the embodiments have no or indeed angiogenesis inhibiting effect.

Dextran sulfate is a sulfated polysaccharide and in particular a sulfated glucan, i.e. polysaccharide made of many glucose molecules. Average molecular weight as defined herein indicates that individual sulfated polysaccharides may have a molecular weight different from this average molecular weight but that the average molecular weight represents the mean molecular weight of the sulfated polysaccharides. This further implies that there will be a natural distribution of molecular weights around this average molecular weight for a dextran sulfate sample.

Average molecular weight ($M_w$) of dextran sulfate is typically determined using indirect methods such as gel exclusion/penetration chromatography, light scattering or viscosity. Determination of average molecular weight using such indirect methods will depend on a number of factors, including choice of column and eluent, flow rate, calibration procedures, etc.

Average molecular weight ($M_w$):

$$\frac{\sum M_i^2 N_i}{\sum M_i N_i},$$

typical for methods sensitive to molecular size rather than numerical value, e.g. light scattering and size exclusion chromatography (SEC) methods. If a normal distribution is assumed, then a same weight on each side of $M_w$, i.e. the total weight of dextran sulfate molecules in the sample having a molecular weight below $M_w$ is equal to the total weight of dextran sulfate molecules in the sample having a molecular weight above $M_w$.

In an embodiment, the dextran sulfate or the pharmaceutically acceptable derivative thereof has an average molecular weight within a range of 2 000 and 10 000 Da. In another embodiment, the average molecular weight is within a range of 2 500 and 10 000 Da. In a particular preferred embodiment, the average molecular weight is within a range of 3 000 to 10 000 Da.

In an optional, but preferred embodiment, less than 40% of the dextran sulfate molecules have a molecular weight below 3 000 Da, preferably less than 35%, such as less than 30% or less than 25% of the dextran sulfate molecules have a molecular weight below 3 000 Da. In addition, or alternatively, less than 20% of the dextran sulfate molecules have a molecular weight above 10 000 Da, preferably less than 15%, such as less than 10% or less than 5% of the dextran sulfate molecules have a molecular weight above 10 000 Da. Thus, in a particular embodiment, the dextran sulfate has a substantially narrow molecular weight distribution around the average molecular weight.

In a particular embodiment, the average molecular weight of dextran sulfate, or the pharmaceutically acceptable derivative thereof, is within a range of 3 500 and 9 500 Da, such as within a range of 3 500 and 8 000 Da.

In another particular embodiment, the average molecular weight of dextran sulfate, or the pharmaceutically acceptable derivative thereof, is within a range of 4 500 and 7 500 Da.

In a further particular embodiment, the average molecular weight of dextran sulfate, or the pharmaceutically acceptable derivative thereof, is within a range of 4 500 and 5 500 Da.

Thus, in a currently preferred embodiment the average molecular weight of dextran sulfate, or the pharmaceutically acceptable derivative thereof, is preferably approximately 5 000 Da or at least substantially close to 5 000 Da, such as 5 000±500 Da, for instance 5 000±400 Da, preferably 5 000±300 Da or 5 000±200 Da, such as 5 000±100 Da. Hence, in an embodiment, the average molecular weight of dextran sulfate, or the pharmaceutically acceptable derivative thereof, is 4.5 kDa, 4.6 kDa, 4.7 kDa, 4.8 kDa, 4.9 kDa, 5.0 kDa, 5.1 kDa, 5.2 kDa, 5.3 kDa, 5.4 kDa or 5.5 kDa.

In a particular embodiment, the average molecular weight of dextran sulfate, or the pharmaceutically derivative thereof as presented above is average $M_w$, and preferably determined by gel exclusion/penetration chromatography, size exclusion chromatography, light scattering or viscosity-based methods.

In a particular embodiment, dextran sulfate, or the pharmaceutically acceptable derivative thereof, consists, on average, of about or slightly above 5 glucose units and has an average sulfate number per glucose unit of at least 2.0, such as of at least 2.5.

Dextran sulfate is a polyanionic derivate of dextran and contains sulfur. The average sulfur content for dextran sulfate of the embodiments is preferably 15 to 20% and more preferably approximately 17%, generally corresponding to about two sulfate groups per glucosyl residue. In a particular embodiment, the sulfur content of the dextran sulfate is preferably equal to or at least close to the maximum possible degree of sulfur content of the dextran molecules.

In a particular embodiment, dextran sulfate of the embodiments has a number average molecular weight ($M_n$) as measured by nuclear magnetic resonance (NMR) spectroscopy within an interval of 1850 and 2000 Da.

In another particular embodiment, dextran sulfate of the embodiments has on average 5.1 glucose units and an average sulfate number per glucose unit of 2.6 to 2.7, typically resulting in a number average molecular weight ($M_n$) as measured by nuclear magnetic resonance (NMR) spectroscopy within an interval of 1850 and 2000 Da.

Number average molecular weight ($M_n$):

$$\frac{\sum M_i N_i}{\sum N_i},$$

typically derived by end group assays, e.g. NMR spectroscopy or chromatography. If a normal distribution is assumed, then a same number of dextran sulfate molecules can be found on each side of $M_n$, i.e. the number of dextran sulfate molecules in the sample having a molecular weight below $M_n$ is equal to the number of dextran sulfate molecules in the sample having a molecular weight above $M_n$.

The dextran sulfate according to the embodiments can be provided as a pharmaceutically acceptable derivative of dextran sulfate. Such pharmaceutically acceptable derivatives include salts and solvates of dextran sulfate, e.g. a sodium or potassium salt.

Dextran sulfate, or the pharmaceutically acceptable derivative thereof, of the embodiments is preferably administered by injection to the subject and in particular by intravenous (i.v.) injection, subcutaneous (s.c.) injection or (i.p.) intraperitoneal injection, preferably i.v. or s.c. injection. Other parenteral administration routes that can be used include intramuscular and intraarticular injection. Injection of dextran sulfate, or the pharmaceutically acceptable derivative thereof, could alternatively, or in addition, take place directly in, for instance, an ischemic tissue or organ or other site in the subject body, at which angiogenesis and increased blood flow are to take place.

The dextran sulfate, or the pharmaceutically acceptable derivative thereof, of the embodiments is preferably formulated as an aqueous injection solution with a selected solvent or excipient. The solvent is advantageously an aqueous solvent and in particular a buffer solution. A non-limiting example of such a buffer solution is a citric acid buffer, such as citric acid monohydrate (CAM) buffer, or a phosphate buffer. For instance, dextran sulfate of the embodiments can be dissolved in saline, such as 0.9% NaCl saline, and then optionally buffered with 75 mM CAM and adjusting the pH to about 5.9 using sodium hydroxide. Also non-buffered solutions are possible, including aqueous injection solutions, such as saline, i.e. NaCl (aq). Furthermore, other buffer systems than CAM could be used if a buffered solution are desired.

The embodiments are not limited to injections and other administration routes can alternatively be used including orally, nasally, bucally, rectally, dermally, tracheally, bronchially, or topically. The active compound, dextran sulfate, is then formulated with a suitable excipient or carrier that is selected based on the particular administration route.

Suitable dose ranges for the dextran sulfate of the embodiments may vary according to the size and weight of the subject, the condition for which the subject is treated, and other considerations. In particular for human subjects, a possible dosage range could be from 1 µg/kg to 150 mg/kg of body weight, preferably from 10 µg/kg to 100 mg/kg of body weight.

In preferred embodiments, the dextran sulfate, or the pharmaceutically acceptable derivative thereof, is formulated to be administered at a dosage in a range from 0.05 to 50 mg/kg of body weight of the subject, preferably from 0.05 or 0.1 to 40 mg/kg of body weight of the subject, and more preferably from 0.05 or 0.1 to 30 mg/kg, or 0.1 to 25 mg/kg or from 0.1 to 15 mg/kg or 0.1 to 10 mg/kg body weight of the subject.

Administration of dextran sulfate, or the pharmaceutically acceptable derivative thereof, of the embodiments is preferably initiated as soon as possible after injury or other condition causing ischemia, stroke or a cardiovascular disease in the subject or causing a medical condition that could be treated or at least alleviated by angiogenesis induction as triggered by the administration of dextran sulfate, or the pharmaceutically acceptable derivative thereof.

Administration of dextran sulfate, or the pharmaceutically acceptable derivative thereof, does not necessarily have to be limited to treatment of a present medical condition but could alternatively, or in addition, be used for prophylaxis. In other words, dextran sulfate of the embodiments could be administered to a subject that will undergo a medical procedure, such as surgery, that may cause at local ischemia or other medical effect that could be treated, inhibited or alleviated by induction of angiogenesis and/or increasing blood flow.

The dextran sulfate of the embodiments can be administered at a single administration occasion, such as in the form of a single bolus injection. This bolus dose can be injected quite quickly to the patient but is advantageously infused over time so that the dextran sulfate solution is infused over a few minutes of time to the patient, such as during 5 to 10 minutes.

Alternatively, dextran sulfate of the embodiment can be administered at multiple, i.e. at least two, occasions during a treatment period. The duration of such a treatment period is typically related to the endogenous time period of wound healing in different types and the type of insult. For more information of suitable treatment periods, reference can be made to Chapter 1 Overview of Wound Healing in Different Tissue Types, pages 3-40 of Indwelling Neural Implants: Strategies for Contending with the In Vivo Environment, ed. William M. Reichert, 2008 by Taylor & Francis Group, LLC (ISBN: 978-0-8493-9362-4).

Thus, dextran sulfate of the embodiments could be administered once or at multiple times per day, once or at multiple times per week, once or at multiple times per month as illustrative examples.

Generally, for acute diseases, such as causing acute ischemia in, for instance, stroke, myocardial infarction (MI), cell and organ transplantation, the duration of the treatment period could be a single administration but is preferably in the form of several administrations during a treatment period of, for instance, a week, a few weeks, or a month. Longer treatment periods up to three months or even a year can further improve healing and recovery.

For ischemic conditions of intermittent type, there can be an option to use the treatment as prophylaxis (prevention) or treatment directly after exacerbation of the disease. This type of administration protocol could be suitable for diseases such as multiple sclerosis (MS), amytrophic lateral sclerosis (ALS) and sickle cell disease. Treatment periods can be up to 1-3 months for treatment after exacerbation. For prophylaxis of the disease, optionally longer treatment periods can be used.

The induction of angiogenesis in a subject through administration of dextran sulfate, or the pharmaceutically acceptable derivative thereof, of the embodiments is preferably taking place in a human subject suffering from a disease, disorder or medical condition causing ischemia in the body of the human subject.

Ischemia is a restriction in blood supply to tissues, causing a shortage of oxygen and glucose needed for cellular metabolism. Ischemia is generally caused by problems with blood vessels, with resultant damage to or dysfunction of tissue or organ. It also means local anemia and hypoxia in a given part of a body sometimes resulting from congestion, such as vasoconstriction, thrombosis or embolism.

An effective treatment of ischemia or an effective approach in preventing or at least reducing the risk of suffering from ischemia is to induce angiogenesis. The angiogenesis causes an increase in blood flow in the relevant tissue and can thereby counteract any restriction in blood supply to the tissue caused by the disease, disorder or medical condition.

Non-limiting but illustrative examples of diseases, disorders or medical conditions that can cause ischemia include wound healing; peripheral ischemia, such as ischemia following transplantation of organs, tissues or cells, peripheral arterial disease, limb ischemia, restless leg, Raynaud's syndrome, sickle cell disease, or thromboangiitis obliterans; coronary ischemia, such as caused by congestive heart failure, myocardial infarction or coronary arterial disease; ischemic diseases in children, such as perinatal or neonatal diseases, childhood diseases, e.g. neonatal hypoxic or ischemic brain injury, asphyxia encephalopathy, cerebral palsy; ischemia in central nervous system, such as caused by traumatic brain injury, temporal arteritis, hypoxia caused by multiple sclerosis, stroke, amytrophic lateral sclerosis; or muscular dystrophic disease; ischemia caused by thrombotic, hemorrhagic or traumatic injuries.

Wound healing generally involves four phases, typically denoted early phase, inflammatory phase, proliferative phase and maturation and remodeling phase. Angiogenesis is one of the processes taking place during the proliferative phase. Administration of dextran sulfate, or the pharmaceutically acceptable derivative thereof, may promote the angiogenesis effect taking place as one of the sub-processes of wound healing. The process of angiogenesis occurs concurrently with fibroblast proliferation during wound healing when endothelial cells migrate to the area of the wound. Because the activity of fibroblasts and epithelial cells requires oxygen and nutrients, angiogenesis is imperative for other stages in wound healing, like epidermal and fibroblast migration.

Peripheral ischemia generally denotes ischemic states taking place in tissues and organs different from the heart (coronary ischemia) and the central nervous system (CNS ischemia). There can be various causes of peripheral ischemia. A typical example is transplantation of organs or tissue to a subject. The transplanted organ or tissue is then typically exposed to ischemia during the initial engraftment process taking place from the point of transplantation until new blood vessels have been formed around the transplanted organ or tissue. There is a high risk of damage to or dysfunction of the organ or tissue due to ischemia and hypoxia if sufficient blood supply is not established shortly after transplantation. Hence, induction of angiogenesis by dextran sulfate, or the pharmaceutically acceptable derivative thereof, according to the embodiments in connection with transplantation may significantly reduce the risk of damage to or dysfunction of the transplanted organ or tissue due to ischemia and/or hypoxia. Administration of dextran sulfate, or the pharmaceutically acceptable derivative thereof, according to the embodiments can be taking place prior to the transplantation in order to induce angiogenesis and provide increase blood flow at the site of transplantation prior to the actual transplantation event. In such a case, the increase in blood flow induced by dextran sulfate of the embodiments may be sufficient to prevent or at least reduce ischemic damages to the transplanted organ or tissue.

Peripheral vascular disease (PVD), commonly referred to as peripheral artery disease (PAD) or peripheral artery occlusive disease (PAOD) or peripheral obliterative arteriopathy, refers to the obstruction of large arteries not within the coronary, aortic arch vasculature, or brain. PVD can result from atherosclerosis, inflammatory processes leading to stenosis, an embolism, or thrombus formation. It causes either acute or chronic ischemia. An efficient treatment of PVD is to restore blood flow by administration of dextran sulfate, or the pharmaceutically acceptable derivative thereof, according to the embodiments.

Limb ischemia, often referred to as acute limb ischemia, occurs when there is a sudden lack of blood flow to a limb. Acute limb ischemia is typically due to either an embolism or thrombosis. Thrombosis is usually caused by peripheral vascular disease (atherosclerotic disease that leads to blood vessel blockage), while an embolism can be due to air, trauma, fat, amniotic fluid, or a tumor. Subjects suffering from limb ischemia would benefit from administration of dextran sulfate, or the pharmaceutically acceptable derivative thereof, of the embodiments.

In medicine, Raynaud's phenomenon is excessively reduced blood flow in response to cold or emotional stress, causing discoloration of the fingers, toe, and occasionally other areas. Raynaud's phenomenon by itself is just a sign (hypoperfusion) accompanied by a symptom. When linked to pathogenesis, it can be part of Raynaud's disease (also known as primary Raynaud's phenomenon), where the cause is unknown, or part of Raynaud's syndrome (secondary Raynaud's phenomenon), which is a syndrome caused by a known primary disease, most commonly connective tissue disorders such as systemic lupus erythematosus. It is a hyperactivation of the sympathetic nervous system causing extreme vasoconstriction of the peripheral blood vessels, leading to tissue hypoxia. Chronic, recurrent cases of Raynaud phenomenon can result in atrophy of the skin, subcutaneous tissues, and muscle, possibly causing ulceration and ischemic gangrene. Administration of dextran sulfate, or the pharmaceutically acceptable derivative thereof, of the embodiments can be an efficient means of reducing the risk of suffering from, treating or at least alleviating the symptoms of Raynaud's syndrome or disease.

Sickle-cell disease (SCD), or sickle-cell anaemia (SCA) or drepanocytosis, is a hereditary blood disorder, characterized by red blood cells that assume an abnormal, rigid, sickle shape. Sickling decreases the flexibility of the red blood cells and results in a risk of an inadequate flow of blood to a part of the body. Induction of angiogenesis using dextran sulfate, or the pharmaceutically acceptable derivative thereof, of the embodiments can be used to reduce the risk of developing peripheral ischemia in subjects suffering from SCD.

Thromboangiitis obliterans, also known as Buerger's disease or presenile gangrene, is a recurring progressive inflammation and thrombosis (clotting) of small and medium arteries and veins of the hands and feet. Thromboangiitis obliterans may therefore cause ischemia in the hands and feet due to restriction of the blood flow these extremities. Administration of dextran sulfate, or the pharmaceutically acceptable derivative thereof, of the embodiments can be an efficient means to increase blood flow to the hands and feet.

Coronary ischemia is a medical term for not having enough blood through the coronary arteries. Coronary ischemia is linked to heart disease as well as heart attacks. It is also known as cardiac ischemia. Coronary arterial disease (CAD) occurs when fatty substances get stuck to the walls of coronary arteries, which narrows the arteries and constricts blood flow. This causes a lack of oxygen and blood to the heart, which can result in a myocardial infarction (heart attack). CAD causes constriction of arteries, which leads to a lack of blood flowing through the arteries as well as oxygen, a process called atherosclerosis. Atherosclerosis is the most common cause of coronary ischemia. Increasing blood flow in the heart muscle through induction of angiogenesis triggered by administration of dextran sulfate, or the pharmaceutically acceptable derivative of the embodiments may be important to reduce the risk of or reduce the damage caused by coronary ischemia. Also thrombosis may be a cause to coronary ischemia.

Myocardial infarction (MI) or acute myocardial infarction (AMI), commonly known as a heart attack, occurs when blood flow stops to part of the heart causing damage to the heart muscle. Most MIs occur due to coronary artery disease. The mechanism of an MI often involves the rupture of an atherosclerotic plaque leading to complete blockage of a coronary artery. Administration of dextran sulfate, or the pharmaceutically acceptable derivative thereof, of the embodiments reduce the size of infarct size. Accordingly, the permanent damages to the cardiac muscles caused by MI can be significantly reduced according to the embodiments.

Ischemia in CNS may be due to various causes. For instance, traumatic brain injury may cause a blockage or restriction in blood flow to part of the brain. Such a restriction in blood flow may have severe consequences if hypoxia occurs in the brain. Increase in blood flow as caused by administration of dextran sulfate, or the pharmaceutically acceptable derivative thereof, of the embodiments can thereby be used to reduce the risk of permanent damages to the brain caused by ischemia following a traumatic brain injury.

Temporal arteritis, also referred to as giant-cell arteritis (GCA), cranial arteritis or Horton disease, is an inflammatory disease of blood vessels most commonly involving large and medium arteries of the head, predominantly the branches of the external carotid artery. It is a form of vasculitis. Induction of angiogenesis and increase in blood flow as caused by administration of dextran sulfate, or the pharmaceutically acceptable derivative thereof, of the embodiments may be beneficial to subjects suffering from temporal arteritis.

Stroke, sometimes referred to as a cerebrovascular accident (CVA), cerebrovascular insult (CVI) or colloquially brain attack, is the loss of brain function due to a disturbance in the blood supply to the brain. This disturbance is due to either ischemia or hemorrhage. Ischemia is caused by either blockage of a blood vessel via thrombosis or arterial embolism, or by systemic hypoperfusion. Hemorrhagic stroke is caused by bleeding of blood vessels of the brain, either directly into the brain parenchyma or into the subarachnoid space surrounding brain tissue. Subject suffering from a stroke would benefit from a treatment that increases the blood flow to the brain to reduce the risk of damages caused by insufficient blood supply. As a consequence, administration of dextran sulfate, or the pharmaceutically acceptable derivative thereof, of the embodiments is advantageously given to subjects suffering from stroke.

Various neurological disorders may cause a restriction in blood supply to the CNS, such as part of the brain. For instance, *Multiple Sclerosis International* 2013, 1-6 (2013) discloses that early multiple sclerosis (MS) lesions are associated with hypoxia. Hence, subjects suffering from MS may benefit from increased blood flow in order to treat or at least reduce or inhibit hypoxia associated with MS.

Amyotrophic lateral sclerosis (ALS), also referred to as motor neuron disease (MND) and Lou Gehrig's disease, is a neurodegenerative disease with various causes. It is characterized by rapidly progressive weakness due to muscle atrophy and muscle spasticity, difficulty in speaking (dysarthria), swallowing (dysphagia), and breathing (dyspnea). Experiments have shown that ALS is associated with reduction in blood flow in, for instance, premotor frontal lobe regions, *Acta Neurologica Scandinavia* 116, 340-344 (2007). It is speculated that increased blood flow through induction of angiogenesis could be beneficial for subjects suffering from ALS.

Induction of angiogenesis according to the embodiments can further be used in connection with implantation of various medical devices, sensors, etc. where it may be advantageous to induce microcirculation towards or in connection with the implant.

Dextran sulfate of the embodiments can thereby be used to treat, inhibit or prevent various ischemic diseases, disorders and conditions, and also ischemic components in various diseases, disorders and conditions.

Figure 4:
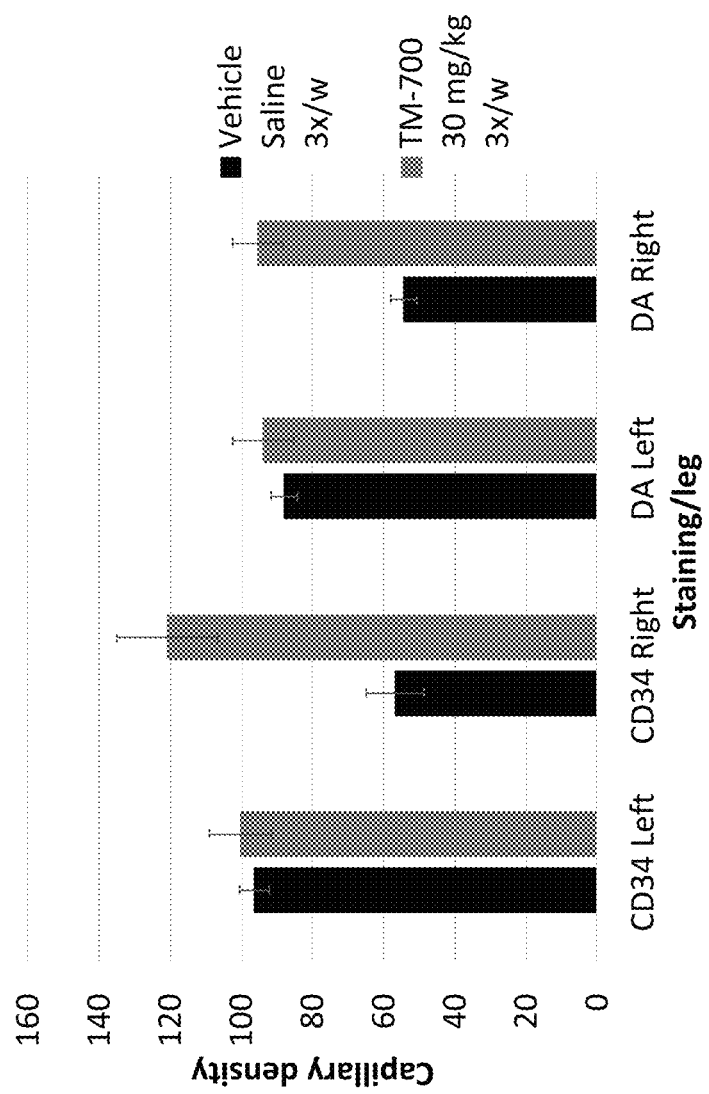
FIG. 4 is a diagram comparing CD34 capillaries density of ischemic and non-ischemic limbs in the groups through the critical limb ischemia study, following double staining with FITC-labeled dextran (DA). DA bars representing functional capillaries. Statistical analysis performed using two-way ANOVA followed by Bonferroni multiple comparisons.
Figure 5A:
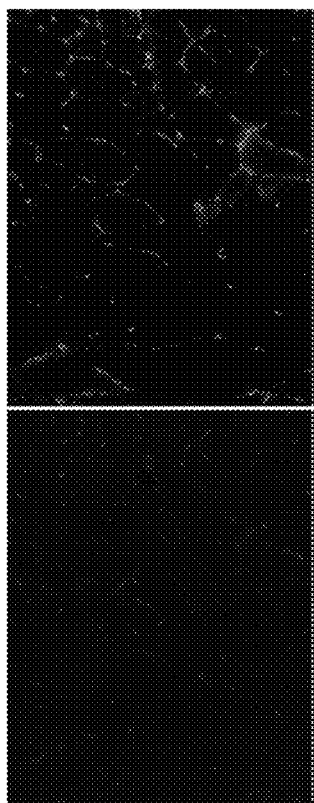
FIGS. 5A-5C illustrate CD34 capillaries density of the groups in the critical limb ischemia study (FIG. 5A—mouse from group 1M vehicle control.
Figure 5B:
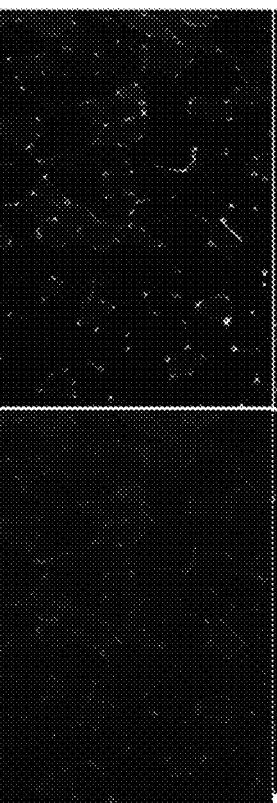
Figure 5C:
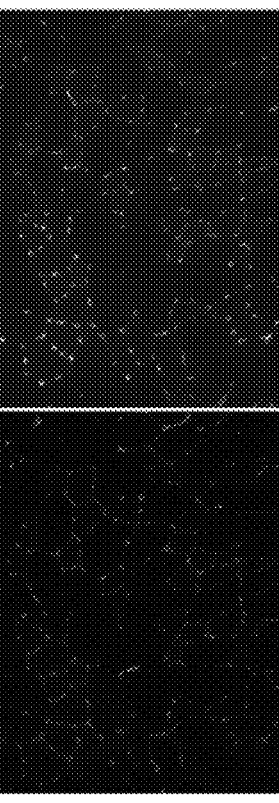

A significant advantage of the present embodiments is that dextran sulfate of the embodiments is capable of selectively inducing angiogenesis in a subject, i.e. induce angiogenesis at a site, such as tissue or organ, where angiogenesis is needed. For instance, angiogenesis is induced and takes place in ischemic tissue but not in non-ischemic tissue as exemplified in FIG. 4 showing the presence of small capillaries formation (as illustrated by CD-34) and confirming functioning and active capillaries (as illustrated by DA) in the ischemic right limb but not in the non-ischemic left limb.

Another aspect of the embodiments relates to a method for inducing angiogenesis in a subject. The method comprises administering dextran sulfate, or a pharmaceutically acceptable derivative thereof, having an average molecular weight below 10 000 Da to the subject.

A further aspect of the embodiments relates to use of dextran sulfate, or a pharmaceutically acceptable derivative thereof, having an average molecular weight below 10 000 Da for the manufacture of a medicament for inducing angiogenesis in a subject.

Yet another aspect of the embodiments relates to dextran sulfate, or a pharmaceutically acceptable derivative thereof, having an average molecular weight below 10 000 Da for use in increasing blood flow in a subject suffering from ischemia.

A related aspect of the embodiments defines a method for increasing blood flow in a subject suffering from ischemia. The method comprises administering dextran sulfate, or a pharmaceutically acceptable derivative thereof, having an average molecular weight below 10 000 Da to the subject. Another related aspect of the embodiments defines use of dextran sulfate, or a pharmaceutically acceptable derivative thereof, having an average molecular weight below 10 000 Da for the manufacture of a medicament for increasing blood flow in a subject suffering from ischemia.

In a particular embodiment, dextran sulfate, or the pharmaceutically acceptable derivative thereof, is capable of increasing blood flow in an ischemic tissue or organ of the subject.

The tissue or organ can be a peripheral organ, the heart or CNS tissue, such as the brain, as discussed in the foregoing.

Still another aspect of the embodiments relates to dextran sulfate, or a pharmaceutically acceptable derivative thereof, having an average molecular weight below 10 000 Da for vascularizing ischemic tissue in a subject.

A related aspect of the embodiments defines a method for vascularizing ischemic tissue in a subject. The method comprises administering dextran sulfate, or a pharmaceutically acceptable derivative thereof, having an average molecular weight below 10 000 Da to the subject. Another related aspect of the embodiments defines use of dextran sulfate, or a pharmaceutically acceptable derivative thereof, having an average molecular weight below 10 000 Da for the manufacture of a medicament for vascularizing ischemic tissue in a subject.

The ischemic tissue could be a peripheral organ, the heart or CNS tissue, such as the brain, as discussed in the foregoing.

The vascularization, i.e. formation of small capillaries, induced or triggered by dextran sulfate of the embodiments is selective in terms of taking place in ischemic tissue in a subject but not in non-ischemic, i.e. healthy, tissue of the subject. The vascularization induced according to the embodiments thereby occurs at the site(s) where it is needed while leaving healthy tissue unaffected (no significant vascularization formation).

The subject is preferably a mammalian subject, more preferably a primate and in particular a human subject. The present embodiment can, however, be used also in veterinary applications. Non-limiting example of animal subjects include primate, cat, dog, pig, horse, mouse, rat.

The embodiments may also be applied to in vitro and/or ex vivo treatment of vascularized tissue and/or organs in order to induce angiogenesis in the vascularized tissue and/or organ, increase blood flow in the vascularized tissue and/or organ and/or vascularizing a vascularized tissue and/or organ.

In such a case, the dextran sulfate, or a pharmaceutically acceptable derivative thereof, can be added to the vascularized tissue and/or organ in various in vitro or ex vivo applications. For instance, dextran sulfate, or a pharmaceutically acceptable derivative thereof, can be added to a culture medium in which the vascularized tissue and/or organ is immersed or contacted in vitro. Alternatively, or in addition, the vascularized tissue and/or organ could be sprayed with a solution comprising dextran sulfate, or a pharmaceutically acceptable derivative thereof. Furthermore, if the vascularized tissue and/or organ is connected to an extracorporeal circulation pump or extracorporeal membrane oxygenation (ECMO) device, then dextran sulfate, or a pharmaceutically acceptable derivative thereof, could be added to the blood that is pumped through the vascularized tissue and/or organ.

EXPERIMENTS

Example 1

Evaluation of Angiogenesis in Critical Hind-Limb Ischemia Mouse Model

Peripheral artery disease (PAD) is a form of peripheral vascular disease (PVD) in which there are partial or total blockage of blood supply to a limb, usually the leg, leading to impaired blood flow and hypoxia in the tissue. When PAD advances it reaches the stage of critical limb ischemia (CLI) with skin ulcerations, gangrene and unavoidable amputations. Therapeutic angiogenesis emerged as a non-invasive means of promoting neovascularization in ischemic tissues. As disclosed in the present study systemic subcutaneous administration of dextran sulfate promote angiogenesis causing formation of small blood vessels and proliferation of endothelial cells. In the present study a stable severe ischemia model (*Journal of Experimental and Clinical Medicine* 31, 128-132 (2006)) was applied to assess safety and efficacy of dextran sulfate on angiogenesis and functional outcome.

Materials

Dextran sulfate with an average molecular weight within a range of 5-7 kDa was obtained from pK Chemicals A/S, Denmark. In FIGS. 1-4, 6, 7 dextran sulfate is denoted TM-700.

An injection solution of dextran sulfate was prepared the day before start of the study. As vehicle, 0.9% NaCl (saline) (Teva Pharmaceutical Industries Ltd) was used. The injection solution was prepared by adding the relevant volume of NaCl to the weighed compound to obtain a target concentration for administration (10 or 30 mg/kg body weight). The dextran sulfate was dissolved by vortexing or simply by turning the tube a few times. The solution was stored at 2-8° C. over night for aggregates to stabilize. The next day, the tube was vortexed and the solution was filtered through a 0.2 µm filter to obtain a sterile solution. Solutions were prepared at day 7, to use at days 8-21, and a second preparation was performed at day 21, to be used at days 22-35. The solution was stored at 2-8° C. between application dates.

In total 60 male Balb/c mice, 9 weeks old, having an average body weight of 24.7 g at study initiation (day 0) were obtained from Harlan Laboratories, Israel. The minimal and maximal weight recorded in each group was within the range of ±20% of the group mean. Animals were handled according to the National Institute of Health (NIH) and the Association for Assessment and Accreditation of Laboratory Animal Care (AAALAC). Animals were housed in polysufone (PSU) cages (5/cage) measuring 42.5×265.6×18.5 cm, with stainless steel top grill having facilities for pelleted food and drinking water in glass-clear polycarbonate bottle; bedding: steam sterilized clean paddy husk (Harlan, Sani-chip, Cat #: 106S8216) was used and bedding material was changed along with the cage at least twice a week. Animals were fed ad libitum a commercial rodent diet (Teklad Certified Global 18% Protein Diet cat #: 106S8216). Animals had free access to autoclaved and acidified drinking water (pH between 2.5 and 3.5) obtained from the municipality supply. Animals were housed under standard laboratory conditions, air conditioned and filtered (HEPA F6/6) with adequate fresh air supply (minimum 15 air changes/hour). Animals were kept in a climate controlled environment. Temperatures range was 20-24° C. and RH range was 30-70% with 12 hours light and 12 hours dark cycle.

Surgical Procedure

On the day of surgery anesthesia was induced by 1.5 to 3.0% isoflurane, 1.5% $N_2O$ and 0.5% $O_2$. Under anesthesia, the mice were placed with ventral side up. A 0.5-1.0 cm incision was made in the skin in the inguinal area. The femoral artery was ligated proximally just after the distal part of the iliac artery and distally after its bifurcation with profound femoral artery with 6-0 silk thread, transected and excised between two ligatures. The wound was closed with 4-0 silk thread and the mice were allowed to recover.

Dextran Sulfate Treatment

On day 8, week 2 post-surgery, each animal in groups 2M and 3M were injected dextran sulfate solution s.c. three times a week. Animals in group 4M were injected s.c. once a week and group 1M received vehicle treatment (NaCl), see Table 1.

TABLE 1

Group allocation

| Group | Treatment | Volume | Route of administration |
|---|---|---|---|
| 1M (n = 15) | Vehicle control | 10 ml/kg | s.c. repeated three times a week |
| 2M (n = 15) | Dextran sulfate 10 mg/kg | | |
| 3M (n = 15) | Dextran sulfate 30 mg/kg | | |
| 4M (n = 15) | Dextran sulfate 30 mg/kg | | s.c. repeated once a week |

Body Weigh Measurements

Body weight was measured on study day −1 prior to surgery and once a week thereafter. Between day 0 and day 7 a small reduction in mean body weight was observed in all animal groups 1M, 2M, 3M and 4M ranging from 1.1 g to 1.6 g, see FIG. 1. From day 14 onwards a gradual increase in weight was observed. Accordingly, between day 0 and day 35 the mean increase in body weight ranged between 0.4 g to 1.7 g, see Table 2.

TABLE 2

Mean change from baseline in body weight by study group

| Group | Treatment | Mean weight change from day 0 to day 35 (g) |
|---|---|---|
| 1M | Vehicle 3 times/week | 0.4 |
| 2M | Dextran sulfate 10 mg/kg 3 times/week | 1.0 |
| 3M | Dextran sulfate 30 mg/kg 3 times/week | 1.7 |

TABLE 2-continued

Mean change from baseline in body weight by study group

| Group | Treatment | Mean weight change from day 0 to day 35 (g) |
|---|---|---|
| 4M | Dextran sulfate 30 mg/kg 1 time/week | 1.0 |

Blood Flow Measurements

Blood flows in legs from both sides were measured with a non-contact laser Doppler before surgery on day −1 and on days: 1, 7, 14, 21, 28 and 35 post operation. Blood flow measurements was expressed as the ratio of the flow in the ischemic limb to that in the normal limb.

Figure 2:
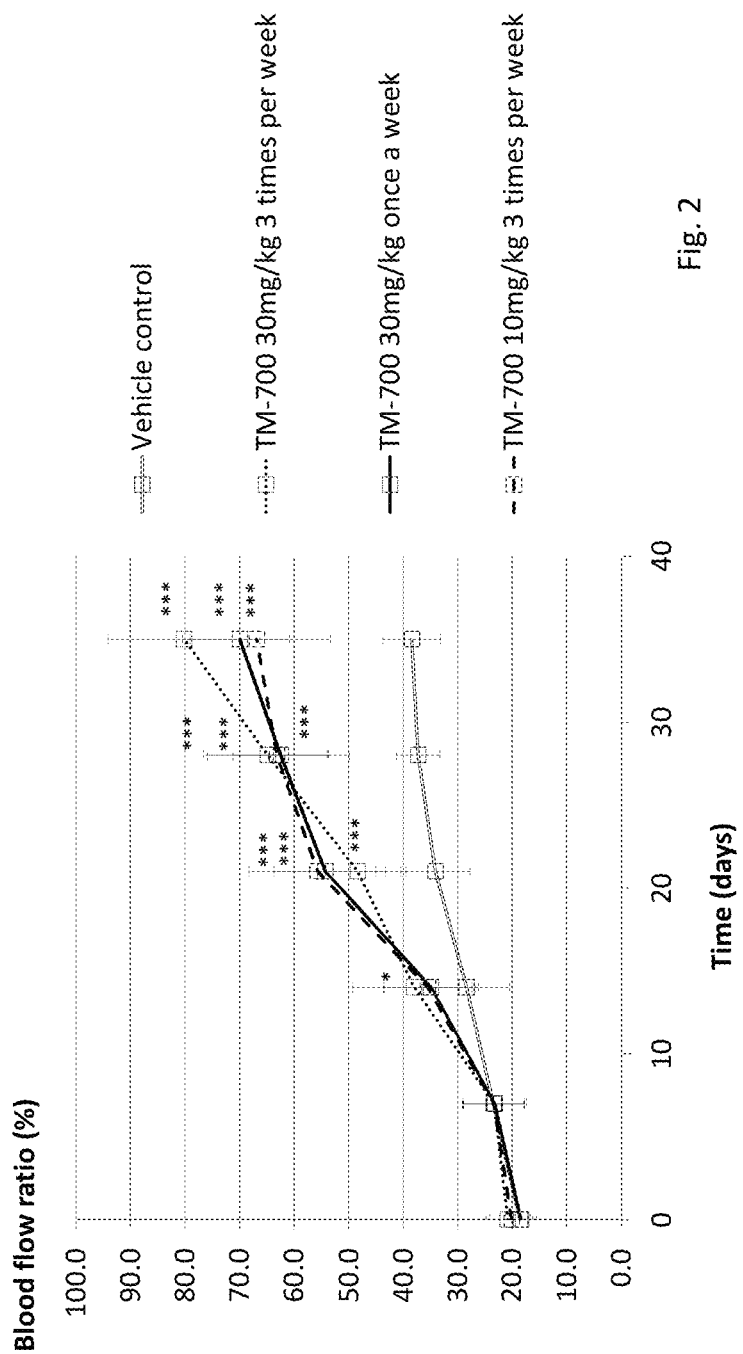
FIG. 2 is a diagram illustrating mean blood flow by study group throughout the mouse critical limb ischemia model. Two-way ANOVA for repeated measures, followed by Bonferroni post-hoc test was performed. Comparison of dextran sulfate treated groups 2M, 3M and 4M to control group 1M revealed statistically significant differences from days 14 and 21 through day 35 ($p<0.001$).
Figure 3:
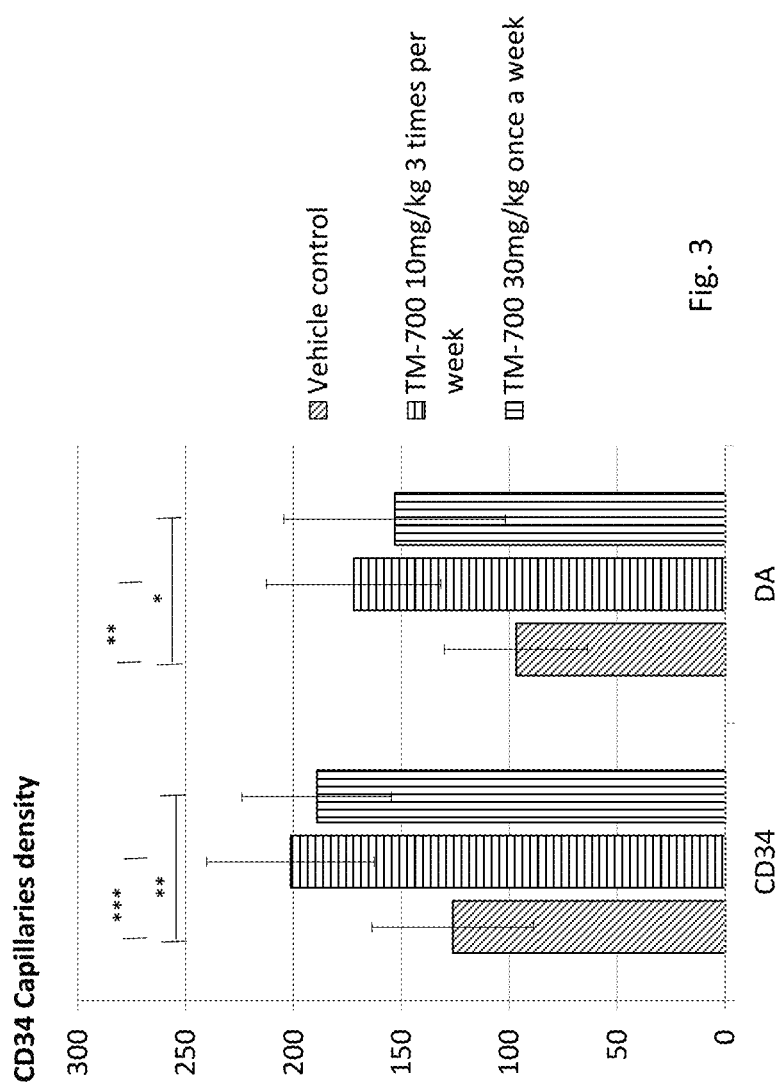
FIG. 3 is a diagram illustrating CD34 capillaries density of the groups through the critical limb ischemia study, following double staining with FITC-labeled dextran (DA). DA bars representing functional capillaries. Statistical analysis performed using two-way ANOVA followed by Bonferroni multiple comparisons.

All animal groups 1M, 2M, 3M and 4M exhibited an increase in mean blood flow in the operated limb between day 1 and day 35, see FIG. 2. The mean blood flow increased from the baseline after surgery in the dextran sulfate treated group 2M (10 mg/kg 3 times/week) by 46.7 units; in the dextran sulfate treated group 3M (30 mg/kg 3 times/week) by 59.3 units and in the dextran sulfate treated group 4M (30 mg/kg 1 time/week) by 51.1 units compared to increase of 19.5 units in the vehicle control group 1M. This represents 2.2, 3.0 and 2.8 folds increase respectively in the mean blood flow due to dextran sulfate treatment, see Table 3 and FIG. 2.

TABLE 3

Mean change in blood flow by study group

| Group | Treatment | Mean change in blood flow day 35 vs. day 1 |
|---|---|---|
| 1M | Vehicle 3 times/week | 19.5 |
| 2M | Dextran sulfate 10 mg/kg 3 times/week | 46.7 |
| 3M | Dextran sulfate 30 mg/kg 3 times/week | 59.3 |
| 4M | Dextran sulfate 30 mg/kg 1 time/week | 51.1 |

FIG. 8 compares blood flow measured in a control mouse (group 1M) and a mouse treated with dextran sulfate according to group 3M. The figure shows non-contact laser Doppler images 35 days after femoral artery ligation of the left hind limb.

Macroscopic Evaluation of Ischemic Severity

Macroscopic evaluation of the ischemic limb was performed on day 7 and once a week thereafter by using morphological grades for necrotic area, see Table 4.

TABLE 4

Morphological grades for necrotic area

| Grade | Description |
|---|---|
| 0 | absence of necrosis |
| 1 | necrosis limiting to toe (toe loss) |
| 2 | necrosis extending to a dorsum pedis (foot loss) |
| 3 | necrosis extending to crus (knee loss) |
| 4 | necrosis extending to a thigh (total hind-limb loss) |

The ischemic limb was macroscopically evaluated weekly from day 7 up to day 35 by using graded morphological scales for necrotic area, see Table 4. In all animal groups treated with vehicle and dextran sulfate toe necrosis or foot amputation was found (graded from 1 to 2, see Table 6). Percent rates of foot amputation in each treatment group are displayed in Table 5 and Table 6. Foot amputation was found in vehicle treated control group 1M (15.4%) and in dextran sulfate treated group 4M (30 mg/kg 1 time/week) (7.1%). Toe necrosis rate in vehicle treated control group 1M was found to be 23.1% animals. In animal groups treated by dextran sulfate 2M and 3M, 35 days after HLI induction toe necrosis rate was 21.4% and 14.3% respectively. In animal group 4M treated by dextran sulfate no incidence of toe necrosis occurred (Table 6).

TABLE 5

Incidence of mice with toe and limb necrosis on day 7

| Group | Incidence of mice with toe necrosis (%) | Incidence of mice with limb amputation (%) |
|---|---|---|
| 1M | 7.6 | 0.0 |
| 2M | 0.0 | 0.0 |
| 3M | 0.0 | 0.0 |
| 4M | 0.0 | 0.0 |

TABLE 6

Incidence of mice with toe and limb necrosis on day 35

| Group | Incidence of mice with toe necrosis (%) | Incidence of mice with limb amputation (%) |
|---|---|---|
| 1M | 23.1 | 15.4 |
| 2M | 21.4 | 0.0 |
| 3M | 14.3 | 0.0 |
| 4M | 0.0 | 7.1 |

In Vivo Assessment of Limb Function and Ischemic Damage

Semi-quantitative assessment of impaired use of the ischemic limb was performed once a week post-surgery using the following scale, see Table 7.

TABLE 7

Assessments of limb function

| Grade | Description |
|---|---|
| 0 | flexing the toe to resist gentle traction of the tail |
| 1 | plantar flexion |
| 2 | no dragging but no plantar flexion |
| 3 | dragging of foot |

Limb function was graded as "Not applicable" in case of partial or full limb amputation. In such case blood flow measurements was not included in the statistical analysis.

Figure 6:
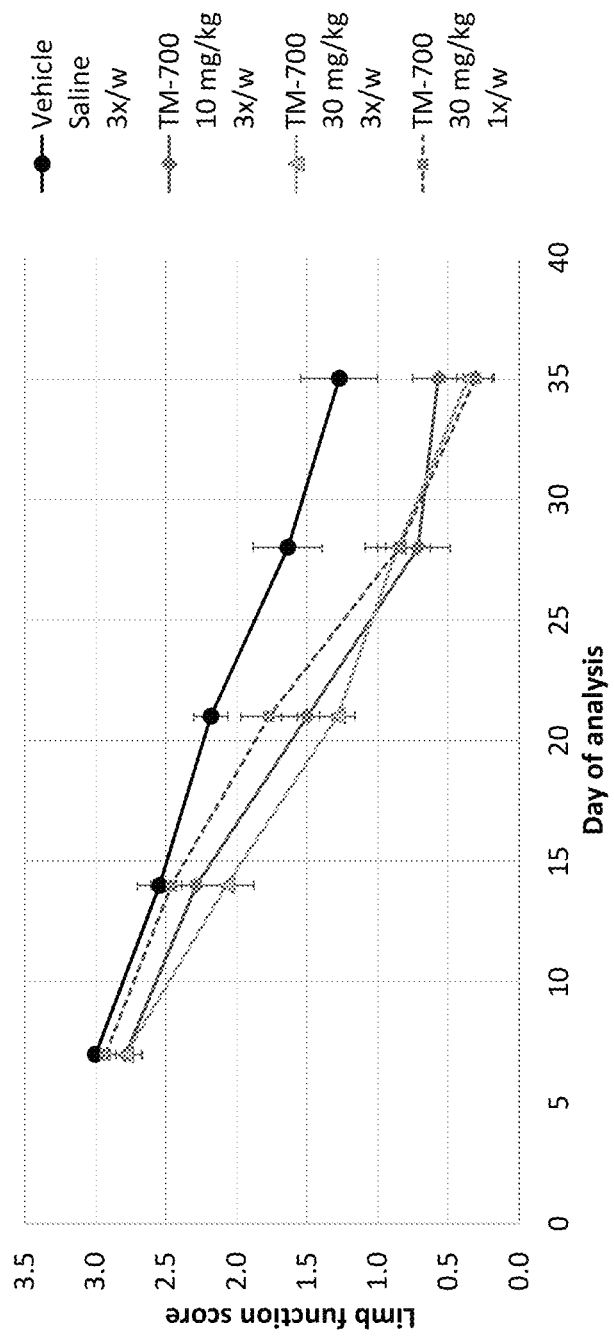
FIG. 6 is a diagram illustrating limb function score in HLI-injured animals treated with dextran sulfate. On day 0, HLI was induced by ligation and excision of the femoral artery. Treatment started on day 8 with once a week (1×/w) or 3 times per week (3×/w) of vehicle or 10 or 30 mg/kg dextran sulfate. Limb score was graded 0-3 where 3 is the worst (dragging of foot). Dextran sulfate induced significant improvement from day 21 and onward (analysis on days 7, 14, 21, 28 and 35), calculated by two-way ANOVA.
Figure 7:
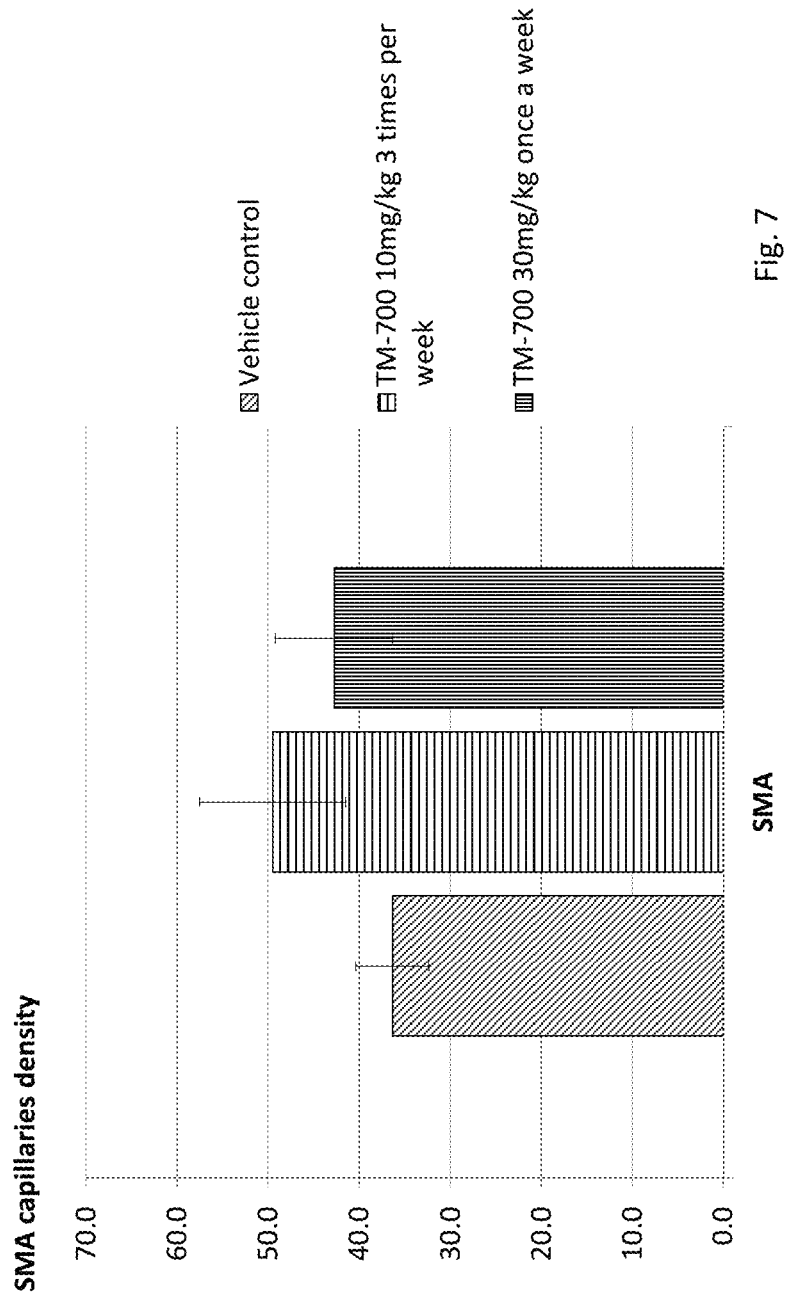
FIG. 7 is a diagram illustrating capillaries density of the groups in the critical limb ischemia study of the endothelial marker smooth muscle actin (SMA). Statistical significance according to two-way ANOVA followed by Bonferroni multiple comparisons.

In parallel to the blood flow measurements and in comparison to the vehicle control group 1M, all dextran sulfate treated groups 2M, 3M and 4M exhibited better results in limb functional improvement, see Table 8 and Table 9 below and FIG. 6.

TABLE 8

Incidence of mice with limb function scores 0, 1, 2 and 3 on day 7

| Group | Incidence of mice with limb function score 0 (%) | Incidence of mice with limb function score 1 (%) | Incidence of mice with limb function score 2 (%) | Incidence of mice with limb function score 3 (%) |
|---|---|---|---|---|
| 1M | 0.0 | 0.0 | 0.0 | 100.0 |
| 2M | 0.0 | 0.0 | 21.4 | 79.6 |
| 3M | 0.0 | 0.0 | 21.4 | 79.6 |
| 4M | 0.0 | 0.0 | 7.1 | 92.9 |

TABLE 9

Incidence of mice with limb function scores 0, 1, 2 and 3 on day 35

| Group | Incidence of mice with limb function score 0 (%) | Incidence of mice with limb function score 1 (%) | Incidence of mice with limb function score 2 (%) | Incidence of mice with limb function score 3 (%) |
|---|---|---|---|---|
| 1M | 9.1 | 72.7 | 0.0 | 18.2 |
| 2M | 50.0 | 42.9 | 7.1 | 0.0 |
| 3M | 72.4 | 21.5 | 7.1 | 0.0 |
| 4M | 69.2 | 30.8 | 0.0 | 0.0 |

Immunohistochemistry and Analysis of Capillaries Density

Mice were sacrificed at study termination on day 36. Fluorescein isothiocyanate (FITC)—dextran 500000 Da conjugate 10 mg/ml was injected i.v. in a dose of 200 μl per mouse 5 minutes before sacrifice to all animals. Quadriceps muscle was dissected into coronary part. The muscle was fixed in 2.5% fresh paraformaldehyde (pH 7.4) for 24 hours and was then embedded in the paraffin for smooth muscle actin (SMA) with mouse monoclonal antibodies (anti-SMA Ab-1, clone 1A4, 1:800, Thermo scientific) and CD34 with anti CD34 (1:200, Cedralene) immunostaining. Paraffin embedding was done according the standard embedding procedure.

Stained sections were evaluated and photographed by fluorescence microscope (E600; Nikon, Tokyo, Japan) equipped with plan fluor objectives connected to a CCD camera (DMX1200F; Nikon). Under these conditions Cy3 shows bright red fluorescence: Ex (max): 543 nm; Em (max) 570 nm while fluorescein dextran shows intense green fluorescence (Ex (max): 488 nm; Em (max): 530 nm). Digital images were collected and analyzed using Image Pro+ software. Four sections of muscle samples were taken from the same areas of eight animals from groups 1M, 3M and 4M. The area of blood vessels was measured. Density was expressed as the mean number of capillaries per field of view. Total vessels represent all blood vessels in the measured area.

The number of CD34 positive capillaries was larger in dextran sulfate treated groups 3M and 4M compared to the control group 1M on day 35 of the study, see FIGS. 3, 4 and 5A-5C. CD34 positive staining is considered as an indication for small capillaries formation, and thus the obtained results support blood flow improvement observed in the animal groups treated with dextran sulfate. Dextran staining confirmed that these capillaries are functioning and active. SMA staining revealed the same increase in capillaries formations as CD34 staining, see FIG. 7.

FIG. 4 clearly shows that dextran sulfate of the embodiments only induce angiogenesis in the ischemic tissue, i.e. in the right limb, and not in the non-ischemic tissue, i.e. the left limb. Thus, dextran sulfate of the embodiments causes a selective induction of angiogenesis only where it is needed.

Impaired angiogenesis is one of the features of ischemic diseases. The most established target for therapeutic angiogenesis has been VEGF and its receptors. However, clinical trials to alleviate ischemia were disappointing, indicating the need for new therapeutic targets to treat ischemic diseases.

In the present study blood flow improvement in the mouse hind-limb ischemia model was examined in order to evaluate the efficacy of dextran sulfate. Repeated (three times a week) or (once a week) dextran sulfate administration at a dose of 30 mg/kg s.c. significantly restored blood perfusion compared to the vehicle treated control. On day 35, two and a half up to three folds higher blood flow perfusion values were observed in the dextran sulfate treated groups compared to the control group, with statistically significant effect starting fourteen days post treatment.

The collective data of the study confirmed the therapeutic efficacy of dextran sulfate given s.c. for the treatment of occlusive peripheral arterial disease in the Balb/c mouse animal model. Spontaneous amputations or toe necrosis rate also decreased in dextran sulfate treated animals compared to the control group. Dextran sulfate treatment improved limb functional restoration in all the drug treated animal group compared to the vehicle treated control. Dextran sulfate treatment did not cause any adverse effects in the treated animals.

Immunohistochemistry findings confirmed the in vivo results. Collectively the data of this study confirmed the therapeutic efficacy of dextran sulfate for the treatment of occlusive peripheral arterial disease in the mouse model.

Dextran sulfate treatment in mice with hind-limb ischemia resulted in a significant and rapid recovery of blood flow, as measured by the laser Doppler and demonstrated also by decrease of limb ischemic severity and more rapid limb function improvement.

No adverse effect on general health was recorded in any of the groups. These data were confirmed by immunohistochemistry evaluation. The findings reflect changes in blood vessel morphology, i.e. capillaries density increase, and blood vessels angiogenesis.

Example 2

Evaluation of Angiogenesis Efficiency in Rat Stroke Model

The stroke tMCAO rat-model was used to evaluate the efficacy of dextran sulfate treatment. Rats were treated with dextran sulfate for 28 days via subcutaneous injections, starting at two hours after the surgical procedure, either at 30 mg/kg three times a week or at a daily dose of 15 mg/kg. During the study the neurological, motoric and somatosensory functions were monitored in a battery of behavioral tests.

Clear differences were demonstrated between the groups treated with dextran sulfate and the vehicle treated control group. Improvement in motor functions, as evaluated by Neuroscore, stepping test and body swing test, was demonstrated in both drug treated groups. Sensory motor functions also recovered following the dextran sulfate treatment. It is likely that the effect of dextran sulfate treatments should be attributed to their angiogenic activity. This conclusion was supported by an increase in cerebral blood perfusion and Smooth Muscle Actin (SMA) positive capillaries density in the affected hemisphere. Dextran sulfate treatment also reduced inflammatory response compared to the vehicle treated control.

In view of these findings it may be concluded that dextran sulfate treatment clearly improved motor and somatosensory deficits as well as cerebral blood perfusion and angiogenic activity in the rat stroke model.

Stroke is a prominent cause of serious, long-term disability and the third leading cause of death in the United States. Total health costs for disability due to stroke are estimated at 53.6 billion annually. Ischemic strokes comprise over 88% of all strokes, making them the most common type of cerebrovascular injury. Ischemic conditions in the brain cause neuronal death, leading to permanent sensorimotor deficits. It is clear now that immediate treatment for stroke patients is often impossible in the clinical setting. Physicians need new treatment strategies for stroke treatments urgently.

Several animal models have been used to study cerebral ischemia in effort to understand its pathophysiology and to identify therapeutic strategies for minimizing the severity of ischemic damage. Focal ischemia results in localized brain infarction and is induced by middle cerebral artery occlusion (MCAO) in the rat. It has gained increasing acceptance as a model for hemispheric infarction in humans. After MCAO a cortical and striatal infarct with temporal and spatial evolution occurs within the vascular territory supplied by the middle cerebral artery.

In the last decade growing evidence for behavioral assessment in the stroke animal studies have been collected. Functional improvement was found to be highly reliable as a measure for therapeutic efficacy. One of the most promising innovative treatments for vascular complications in stroke is therapeutic angiogenesis, which emerged as a non-invasive mean for promoting neovascularization in ischemic tissues.

In this study the neuroprotective and rehabilitation potential of dextran sulfate was studied in transient MCAO rat-stroke model.

Materials

Dextran sulfate with an average molecular weight within a range of 5-7 kDa was obtained from pK Chemicals A/S, Denmark. In FIGS. 9-16 dextran sulfate is denoted TM-700.

Dextran sulfate was dissolved in 0.9% NaCl (saline) (Teva Pharmaceutical Industries Ltd) to a concentration of 60 mg/ml for the three times a week injection and 30 mg/ml for the daily injection. The formulation is stable for one week. Animals received 0.5 ml/kg, equal to 30 and 15 mg/kg body weight.

In total 46 male SD rats having an average body weight of 342 g at study initiation (Day 0) were obtained from Harlan Laboratories, Israel. The minimal and maximal weight recorded in each group was within a range of ±20% of the group mean weight. Animals were handled according to guidelines of the National Institute of Health (NIH) and the Association for Assessment and Accreditation of Laboratory Animal Care (AAALAC). Animals were housed in polyethylene cages (5/cage) measuring 35×30×15 cm, with stainless steel top grill facilitating pelleted food and drinking water in plastic bottle; bedding: steam sterilized clean paddy husk (Harlan, Sani-chip cat #:2018SC+F) was used and bedding material was changed along with the cage at least twice a week. Animals were fed ad libitum a commercial rodent diet (Teklad Certified Global 18% Protein Diet cat #: 106S8216). Animals had free access to autoclaved and acidified drinking water (pH between 2.5 and 3.5) obtained from the municipality supply. Animals were housed under standard laboratory conditions, air-conditioned and filtered (HEPA F6/6) with adequate fresh air supply (Minimum 15 air changes/hour). Animals were kept in a climate-controlled environment. Temperatures range was 20-24° C. and RH range was 30-70% with 12 hours light and 12 hours dark cycle.

Surgical Procedure

On the day of surgery anesthesia were induced with 4% isoflurane in a mixture of 70% $N_2O$ and 30% $O_2$ and maintained with 1.5-2% isoflurane.

Transient middle cerebral artery occlusion was performed according to the method previously described in *Stroke* 29, 2162-2170 (1998). The right common carotid artery (CCA) was exposed through a midline neck incision and carefully dissected free from surrounding nerves and fascia—from its bifurcation to the base of the skull. The occipital artery branches of the external carotid artery (ECA) were then isolated, and these branches were dissected and coagulated. The ECA was dissected further distally and coagulated along with the terminal lingual and maxillary artery branches, which was then divided. The internal carotid artery (ICA) was isolated and carefully separated from the adjacent vagus nerve, and the pterygopalatine artery was ligated close to its origin with a 5-0 nylon suture (SMI, Belgium). Next a 4-0 silk suture was tied loosely around the mobilized ECA stump, and a 4 cm length of 4-0 monofilament nylon suture (the tip of the suture was blunted by using a flame, and the suture was coated with polylysine, prior to insertion) was inserted through the proximal ECA into the ICA and thence into the circle of Willis, effectively occluding the MCA. The surgical wound was closed and the animals were returned to their cages to recover from anesthesia. Two hours after occlusion rats were re-anesthetized, monofilament was withdrawn to allow reperfusion, surgical wound was closed and rats were returned to their cages.

At one hour post occlusion, animals were subjected to neurological evaluation using the "Neuroscore for exclusion criteria". Only animals with an overall score of 10 were included in the study.

Dextran Sulfate Treatment

Started two hours after occlusion (immediately after reperfusion), animals in groups 2M and 3M (dextran sulfate at doses of 30 mg/kg three times a week or 15 mg/kg daily) and animals in group 1M (vehicle control) were injected subcutaneously, see Table 10.

TABLE 10

Group allocation

| Group | Treatment | Dose | Administration | Treatment duration (days) |
|---|---|---|---|---|
| 1M (n = 13) | Vehicle | 0 | s.c. 3 times a week | 28 |
| 2M (n = 15) | Dextran sulfate | 30 mg/kg | | |
| 3M (n = 15) | Dextran sulfate | 15 mg/kg | s.c daily | |

Data Analysis

Unless specified differently, all statistical analyses were performed using two-way ANOVA for repeated measures, followed by Bonferroni post-hoc comparison tests.

Body Weights

Figure 9:
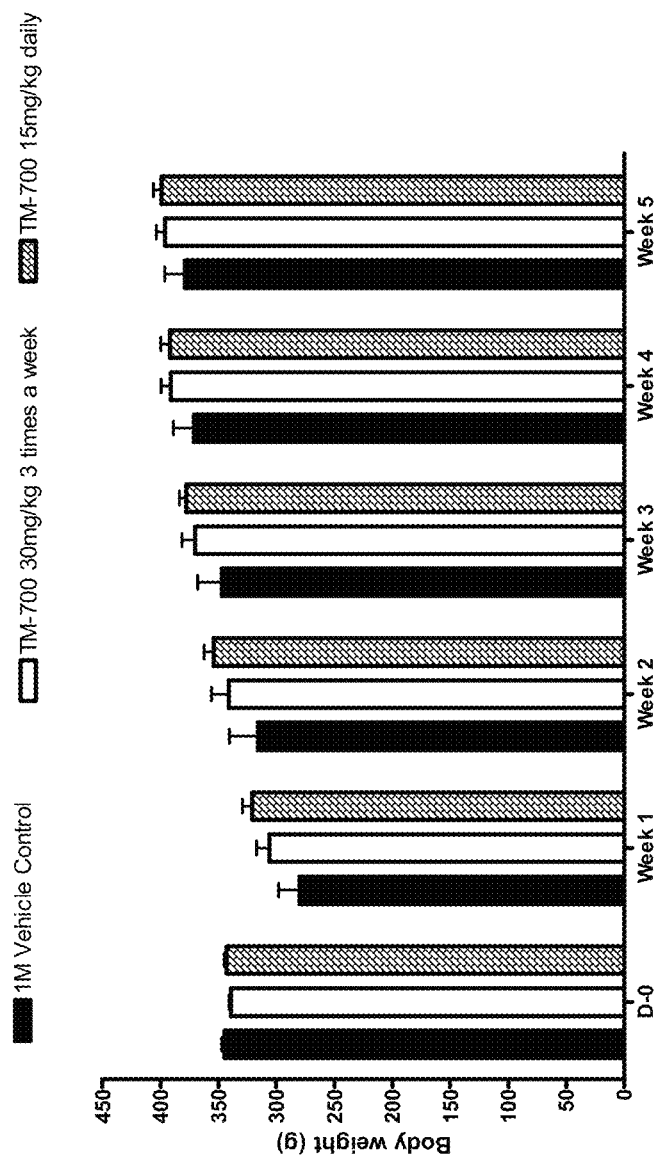
FIG. 9 illustrates distribution of body weight in the groups used for the tMCAO rate-stroke study.

Throughout the study, no statistically significant differences in body weight were observed among the various treatment groups, see FIG. 9.

Neurological Test Score (Neuroscore)

Evaluation: pre-operation, one hour after occlusion and on days 7, 14, 21 and 28

The Modified Neurological Rating Scale (mNRS) was performed. The individual who made the behavioral assessments was unaware of the drug/dose given (blinded test). Neuroscore with total score 18 was performed according to *Stroke* 32, 1005-1011 (2001).

The Neuroscore included a set of clinical-neurological tests (composite of motor, sensory, reflex and balance tests) that were used to assess the effect of the tested treatments. Neuroscore was graded on a scale of 0 to 18 (in which normal score is 0 and maximal deficit score is represented by 18). As expected, in all groups of rats a sharp decline in neurological functions was observed two hours after tMCAO induction, with spontaneous improvement over time thereafter. Statistically significant differences were exhibited in groups 2M treated with 30 mg/kg dextran sulfate three times per week and 3M treated with mg/kg dextran sulfate daily, as compared to the vehicle treated control, from the first test on day 7 throughout the study up to day 28, see FIG. 10. No statistical difference was found between the two dosing schedules 2M and 3M.

Stepping Test

Evaluation: pre-operation and on days 7, 14, 21 and 28

Animals were tested for forelimb akinesia using the stepping test. The animal was held with its hind limbs and one forelimb fixed with one hand and the unrestrained fore-paw was drawn along the table. The number of adjusting steps were counted while the animal was moved sideways along the table surface (85 cm in approximately five seconds), in the forehand and backhand direction for both forelimbs.

Animals were tested for forelimb akinesia in the stepping test, commonly used for measurement of neuromuscular function, as an index for motoric function of the animal. Some improvement in motor function over time was observed in all the animals that were subjected to tMCAO, mostly as a result of spontaneous functional recovery. However, functional improvement in rats treated with dextran sulfate was more pronounced compared to vehicle treated controls. In both treated groups of animals, group 2M and 3M, this improvement reached statistical significance compared to control starting on the first test on day 7 and continued to improve up to study termination on day 28, see FIG. 11. No statistical difference was found between the two dosing schedules 2M and 3M.

Forelimb Placing

Evaluation: pre-operation and on days 7, 14, 21 and 28

For the forelimb-placing test, the examiner holds the rat close to a tabletop and scores the rat's ability to place the forelimb on the tabletop in response to whisker, visual, tactile, or proprioceptive stimulation.

Separate sub-scores were obtained for each mode of sensory input and added to give total scores (0=normal, 12=maximally impaired).

Forelimb placing test (0-12):
Whisker placing (0-2);
Visual placing (forward (0-2), sideways (0-2))
Tactile placing (dorsal (0-2), lateral (0-2))
Proprioceptive placing (0-2).

For each subtest, animals were scored as followed:
0.0=immediate response
0.5=response within 2 seconds
1.0=response of 2-3 seconds
1.5=response of >3 seconds
2.0=no response Forelimb placement test was used to assess somatosensory and sensory motor deficits. Similar to the other tests, some spontaneous improvement in sensory motor deficits over time was observed in all animals that were subjected to tMCAO. However, all rats treated with dextran sulfate exhibited statistically significant improvement compared to vehicle control treatment, starting on day 14 and lasting up to study termination on day 28, see FIG. 12. In group 3M improvement in sensory motor deficits reached statistical significance already at the first testing on day 7.

Body Swing Test

Evaluation: pre-operation and on days 7, 14, 21 and 28

The rat was held approximately one inch from the base of its tail. It was then elevated to an inch above a surface of a table. The rat was held in the vertical axis, defined as no more than 10° to either the left or the right side. A swing was recorded whenever the rat moves its head out of the vertical axis to either side. Before attempting another swing, the rat was returned to the vertical position for the next swing to be counted. Twenty total swings were counted. A normal rat typically has an equal number of swings to either side. Following focal ischemia, the rat tends to swing to the contralateral side (left side in this case). Body swing scores were expressed as a percentage of rightward over total swings. There was a spontaneous partial recovery of body swing scores (toward 50%) during the first month after stroke.

Animals were tested for forelimb akinesia in the body swing test, commonly used for measurement of neuromuscular functions. Some spontaneous improvement in motor function over time was observed in all animals that were subjected to tMCAO. However, all rats treated with dextran sulfate exhibited statistically significant improvement compared to vehicle control treatment, starting on the first test on day 7 and lasting up to study termination on day 28, see FIG. 13. No statistical difference was found between the two dosing groups 2M and 3M.

Cerebral Blood Flow Assessment

Evaluation: day 29

Evaluation of the blood flow on the brain cortex and vessel constriction was carried out using Flow-R Laser Doppler system, in which intracranial blood flow and vessels diameter (constriction/dilatation) was monitored. This was carried out on day 29 post stroke initiation. Doppler procedure was performed while the animals were under isoflurane anesthesia.

Animals were also examined for cerebral blood flow restoration at the damaged hemisphere on day 29. Statistically significant improvement in cerebral blood perfusion rate was observed in all animals that were subjected to tMCAO and treated with dextran sulfate (group 2M and 3M) versus control vehicle-treated group 1M. Vessels diameter ratio also increased in dextran suflate treated animals versus control, see FIGS. 14 and 15.

Samples Collection and Sacrifice

On day 30 after MCAO, rats were anesthetized by ketamine/xylazine were transcardiacly perfused by buffered paraformaldehyde (PFA) 4%. The brains were collected fixed in 4% buffered PFA for immunostaining and histological evaluation.

Two sections of brain samples were taken from the same areas of six animals from groups 1M and 3M. Capillaries were counted under the microscope in a total of three random fields from each section. Density was expressed as the mean number of capillaries per field of view. Treatment with dextran sulfate 15 mg/kg daily increased the number of capillaries 30 days after stroke, as compared to the vehicle treated control group.

Figure 16:
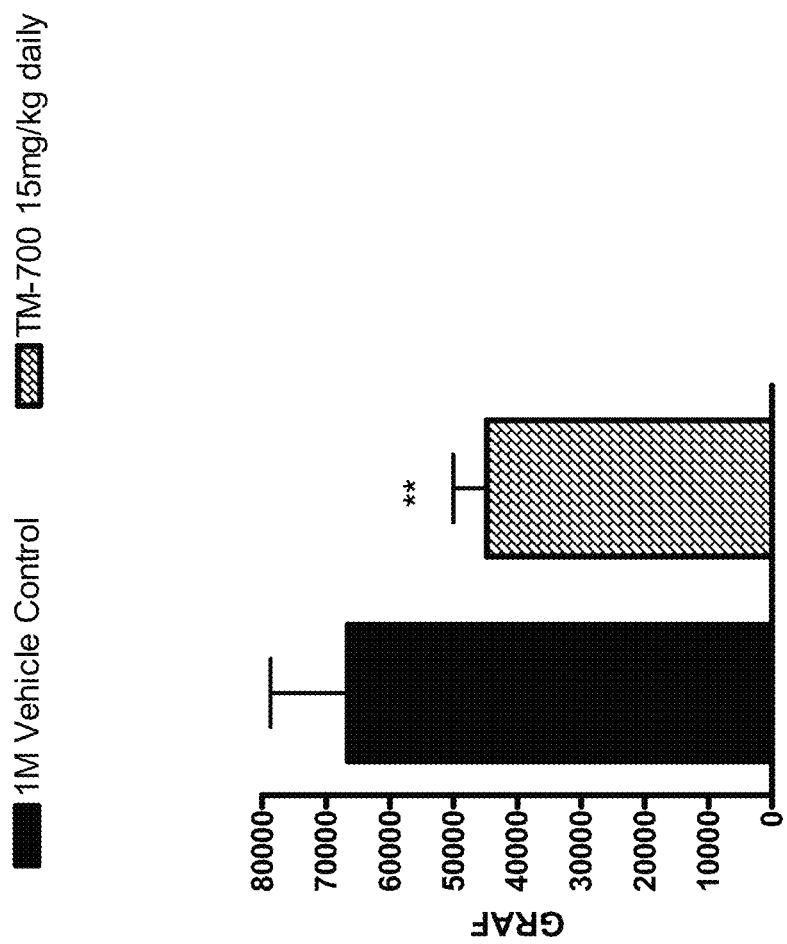
FIG. 16 illustrates GFAP area (area of positive cells in square microns per ×10 field) in dextran sulfate treated group versus control vehicle group on day 30.

Improvement in the number of SMA capillaries with diameter less than 30 µm was observed in animals that were subjected to tMCAO, and treated with dextran sulfate 15 mg/kg daily as compared to vehicle treated control group, as a result of angiogenic effect, see FIG. 16.

Figure 17B:
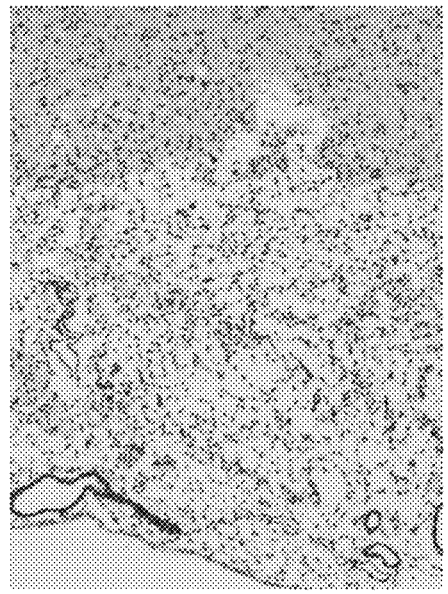
FIGS. 17A and 17B illustrating the treatment effect on capillaries density for a rat from vehicle control group (FIG. 17A) and from dextran sulfate (15 mg/kg, daily) group (FIG. 17B).
Figure 17A:
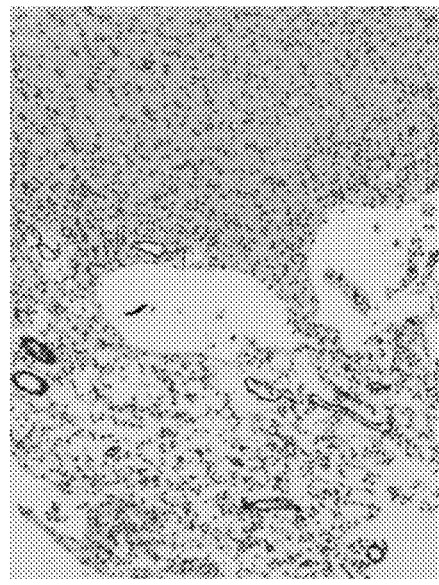

FIGS. 17A and 17B illustrate the treatment effect on capillaries density for a rat from vehicle control group (FIG. 17A) and from dextran sulfate (15 mg/kg, daily) group (FIG. 17B).

Mortality and Clinical Signs

Eighteen rats died during the study. One rat died just after reperfusion before dosing, and seventeen rats within 10 hours after dosing (6 in group 1M, 6 in group 2M and 5 in group 3M). No adverse clinical signs unrelated to the model were observed in all the animal groups.

The stroke tMCAO rat-model is traditionally an accepted model for evaluating the neuroprotective and rehabilitation efficacy of drug treatments. This model was used in the present study to evaluate the efficacy of dextran sulfate treatment at two dosing schedules. Rats were treated with dextran sulfate for 28 days via subcutaneous injections, starting at two hours after the surgical procedure, either at 30 mg/kg three times a week or at a daily dose of 15 mg/kg. During the study the neurological, motoric and somatosensory functions were monitored in a battery of behavioral tests.

Figure 10:
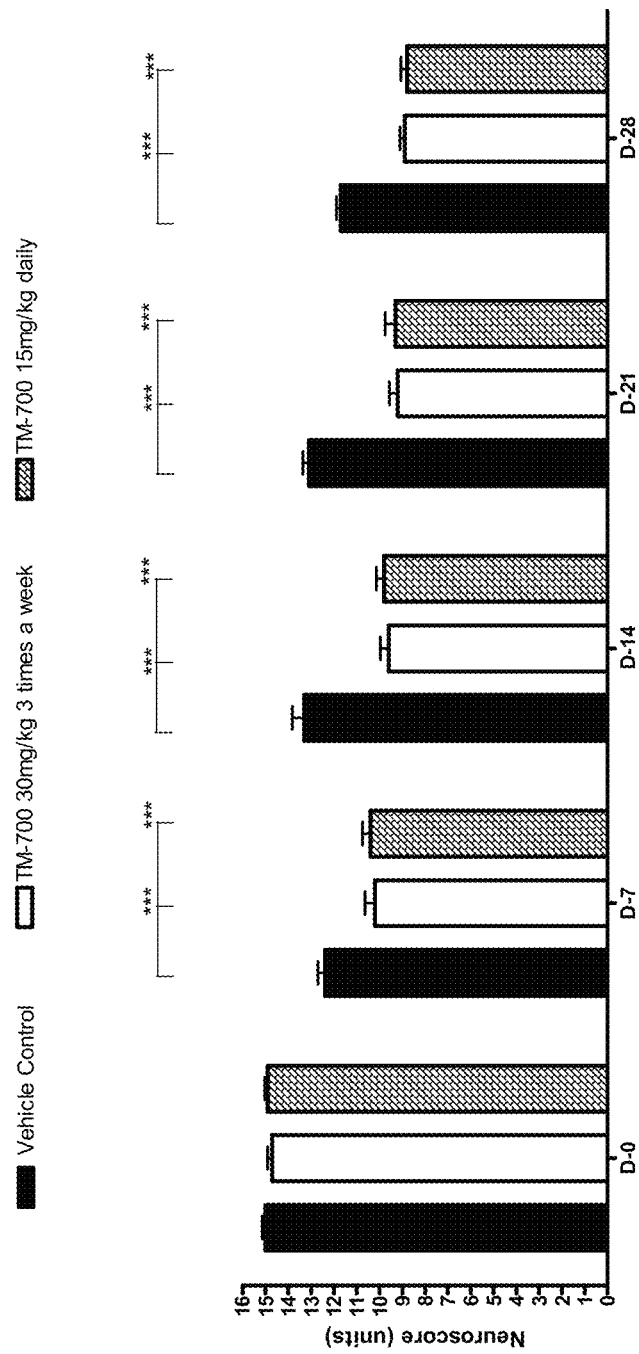
FIG. 10 illustrates Neuroscore by treatment group throughout the tMCAO rate-stroke study.
Figure 11:
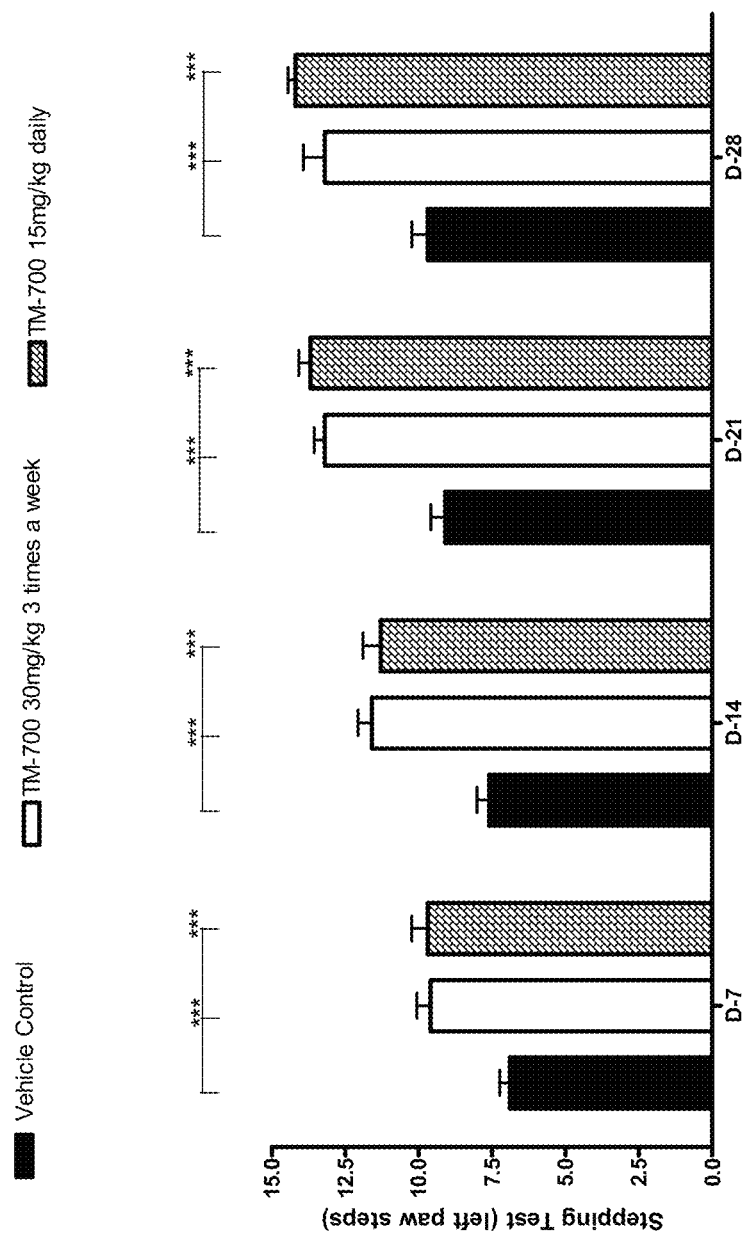
FIG. 11 illustrates stepping test by treatment group throughout the tMCAO rate-stroke study.
Figure 12:
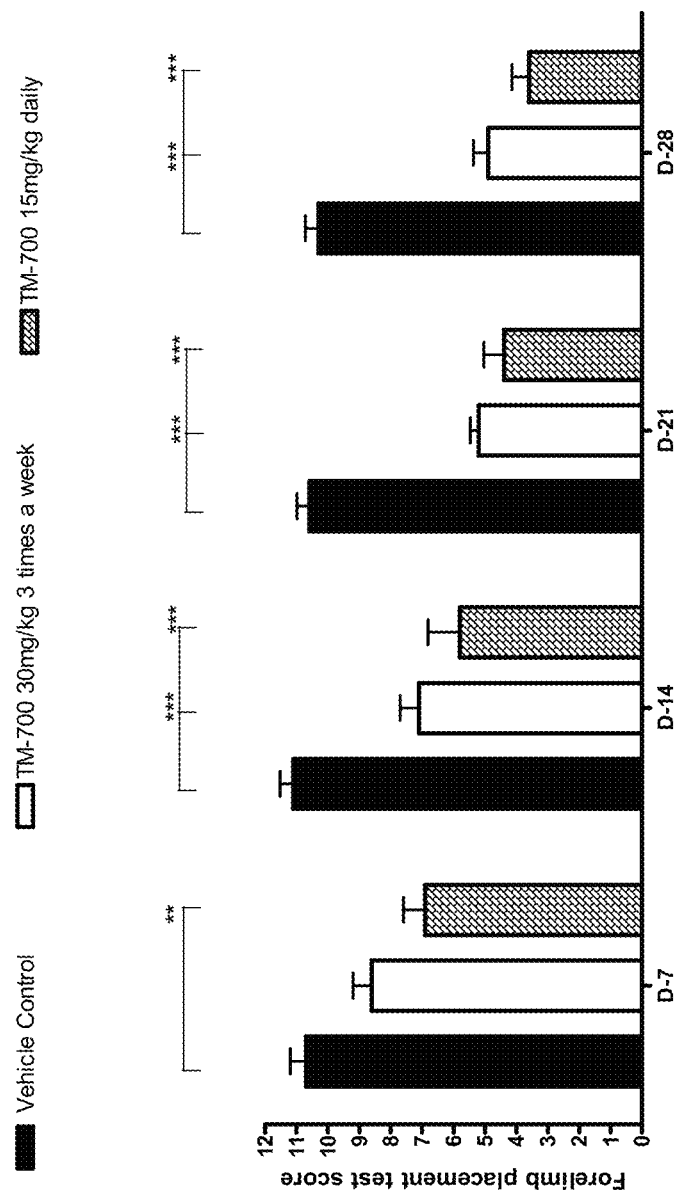
FIG. 12 illustrates forelimb placement test by treatment group throughout the tMCAO rate-stroke study.
Figure 13:
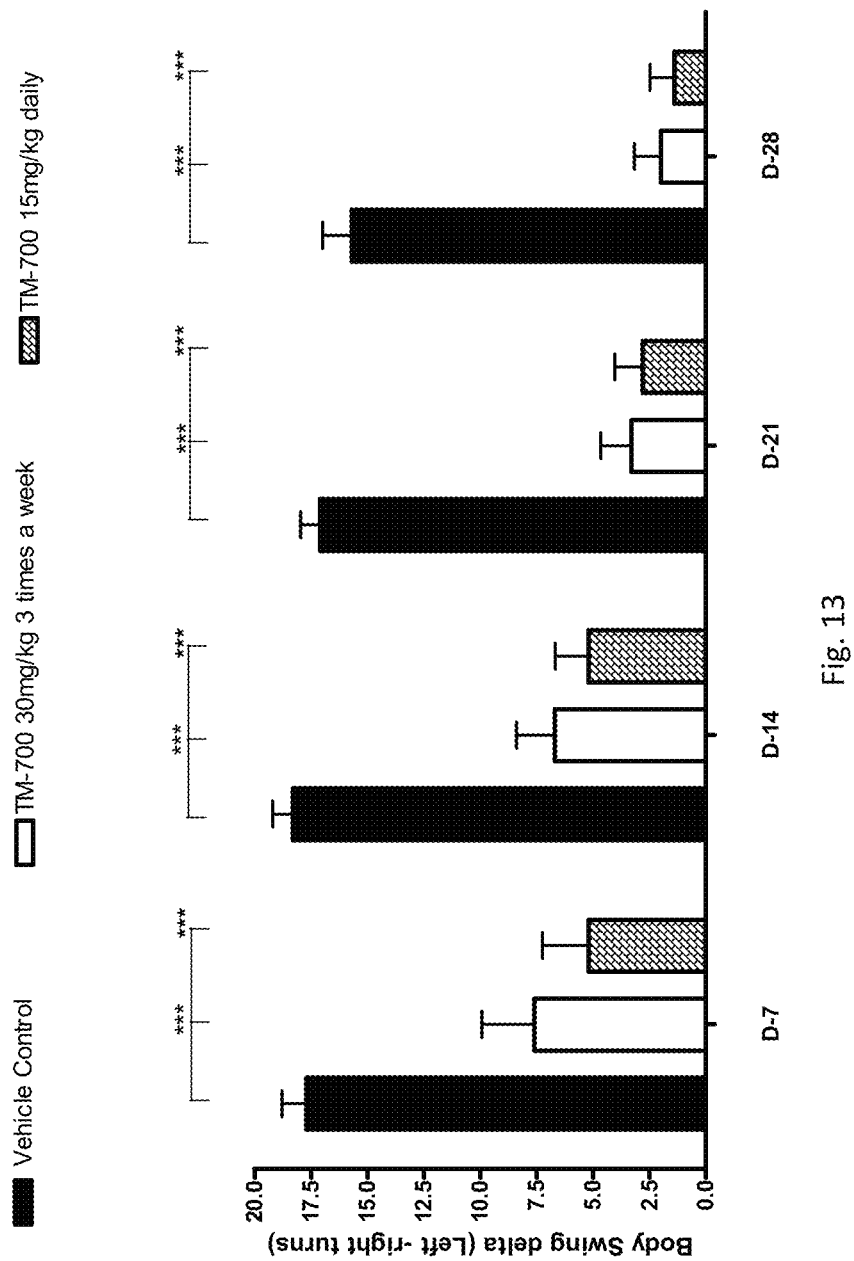
FIG. 13 illustrates body swing test delta (left turn-right turn) by treatment group throughout the tMCAO rate-stroke study.
Figure 14:
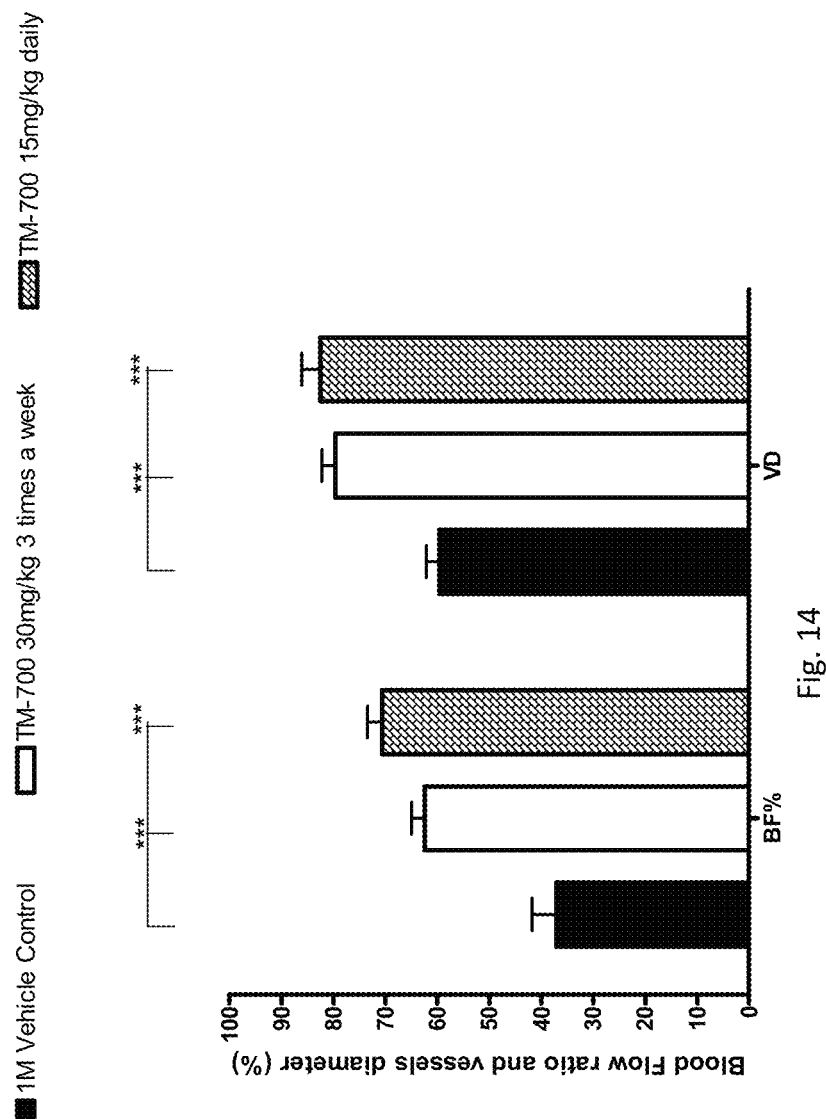
FIG. 14 illustrates cerebral blood flow ratio and percent change of vessels average diameter in both dextran sulfate groups as compared to vehicle control on day 29.
Figure 15:
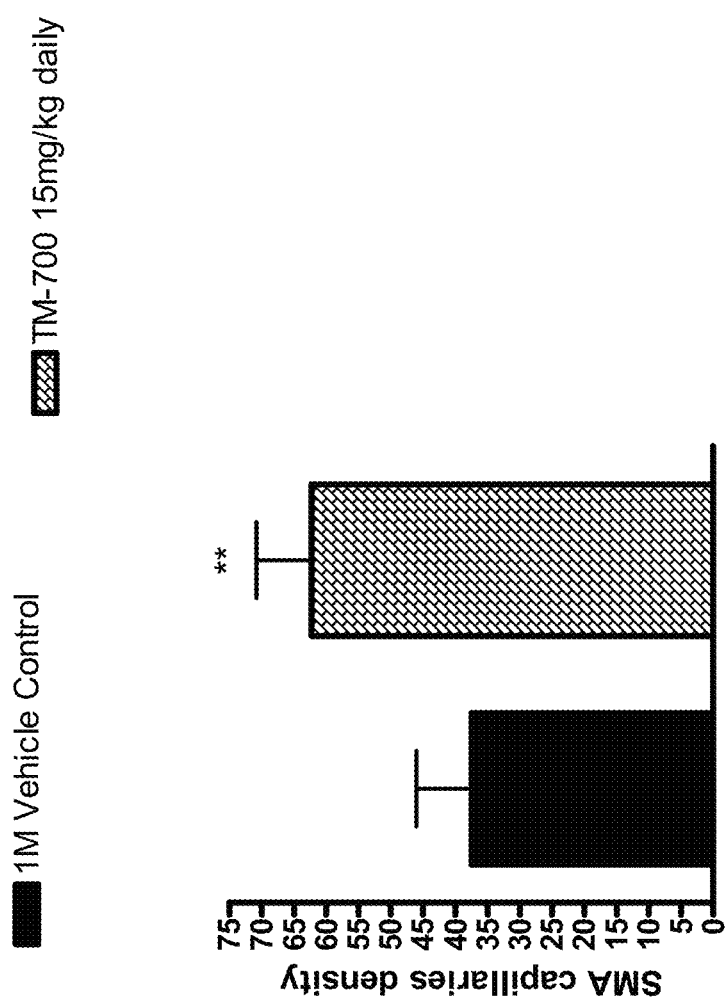
FIG. 15 illustrates SMA capillary density in rats treated by dextran sulfate 15 mg/kg daily as compared to vehicle control on day 30.

As expected, some spontaneous recovery of neurological functions was observed during the 28 days follow-up after stroke induction. However, clear differences were demonstrated between the groups treated with dextran sulfate and the vehicle treated control group. No statistically significant differences were noted however between the two dosing schedules. Improvement in motor functions, as evaluated by Neuroscore, stepping test and body swing test, was demonstrated in both drug treated groups (FIGS. 10, 11 and 13). Sensory motor functions also recovered following the dextran sulfate treatment (FIG. 12). The beneficial effects were observed starting on the first testing on day 7 of the treatment and continued to improve till study termination on day 28. The observed effects cannot be attributed to differences in general rats' health as all groups gained weight at the same rate with no significant differences between them (FIG. 9). In addition, no observed differences in general clinical signs were noted. It is likely that the effect of dextran sulfate treatments should be attributed to their angiogenic activity. This conclusion was supported by an increase in cerebral blood perfusion and SMA positive capillaries density in the affected hemisphere. Dextran sulfate treatment also reduced inflammatory response compared to the vehicle treated control.

In view of these findings it may be concluded that dextran sulfate treatment clearly improved motor and somatosensory deficits as well as cerebral blood perfusion and angiogenic activity in the rat stroke model.

Dextran sulfate of the embodiments has thereby been shown to selectively induce angiogenesis in CLI (Example 1) and stroke (Example 2) models. The experimental results indicate that even a delayed treatment (start day 15 after ligation) is effective. Doses within the interval of 3 to 30 mg/kg (s.c.) are effective and administration protocols of single dose, once weekly and 3 times weekly are all effective. Histology documents newly formed functional vessel formation. The dextran sulfate of the embodiments thereby provides a selective effect in ischemic areas.

Example 3

Evaluation of Dextran Sulfate in a Myocardial Infarction Model

The present study assessed the angiogenic efficacy of dextran sulfate treatment in a rat model of myocardial infarction.

The heart has limited regenerative capacity, so muscle lost to acute myocardial infarction (MI) is typically replaced by non-contractile scar tissue with limited vascularization. Promoting angiogenesis and increase in tissue perfusion is a promising strategy to heart repair after MI.

Materials and Methods

The myocardial infarction model in rat involved ligations of the left coronary artery permanently with an intramural stitch. The surgery caused obstruction of the blood flow and subsequently to severe ischemic damage and cardiac walls infarct.

In total 150 female SD rats having an average body weight of 178 g at study initiation (Day 0) were obtained from Harlan Laboratories, Israel. Animals were fed ad libitum a commercial rodent diet (Teklad Certified Global 18% Protein Diet). Animals had free access to acidified drinking water (pH between 2.5 and 3.5) obtained from the municipality supply. Animals were housed under standard laboratory conditions. Temperatures range was 20-24° C. and RH range was 30-70% with 12 hours light and 12 hours dark cycle.

Dextran sulfate with an average molecular weight within a range of 5-7 kDa was obtained from pK Chemicals A/S, Denmark. Dextran sulfate was dissolved in 0.9% NaCl (saline) (Teva Pharmaceutical Industries Ltd) to be injected subcutaneous at doses of 15 mg/kg or 3 mg/kg.

On the day of surgery the animals were anesthetized with a combination of 90 mg/kg ketamine and 10 mg/kg xylazine. In order to induce MI, under anesthesia and analgesia, the rat chest was opened by left thoracotomy, the pericardium was removed and the proximal left coronary artery was permanently occluyded with an intramural stitch (Circulation 117, 1388-1396 (2008)). Two hours post surgery, each animal in all treated groups were injected s.c. with dextran sulfate or saline vehicle according to Table 11.

TABLE 11

Group allocation

| Group | Treatment | Volume | S.C. Administration |
|---|---|---|---|
| 1M (n = 30) | Vehicle control | 0.5 ml/kg | 3 times a week, starting on day 1 for 3 weeks |
| 2M (n = 30) | Dextran sulfate 15 mg/kg | | 3 times a week, starting on day 1 for 3 weeks |
| 3M (n = 30) | Dextran sulfate 15 mg/kg | | 3 times a week, starting on day 1 for 1 week |
| 4M (n = 30) | Dextran sulfate 15 mg/kg | | single dose on day 1 |
| 5M (n = 30) | Dextran sulfate 3 mg/kg | | 3 times a week, starting on day 1 for 1 week |

On day 36 after MI induction, the rats were sacrificed by $CO_2$ inhalation and the hearts were harvested and fixed in 4% buffered Formalin solution. Routine paraffin embedding was performed using standard histological procedures.

For the purpose of MI size identification, Masson's Trichrome Staining was used. Nine hearts of a treated (2M) group and eight of the untreated (1M) group were sectioned transversely into five sections that were imbedded in paraffin. Five paraffin sections at 5 µm were performed on a Lika microtome. All sections were stained according to standard Masson's trichrome protocol. The sections were visualized in a computer-imaging system and infarct size was marked and calculated using the ImageJ program. Infarct size was expressed as percentage of infarct area (unstained) versus the total left ventricle area. For each animal, five serial sections including one containing the ligature were analyzed and the mean value of all sections for each heart was calculated. Immunohistobchemistry marker (Smooth Muscle Actin—SMA) was used for evaluating the vascular density count.

Vascular density count was performed per 1 mm square on the edge of the infarct lesion of the affected myocardial area. Pictures were taken using an Olympus BX43 microscope using the ×40 objective magnification. Vascular density count of SMA positive vessels was performed using Image Analysis software—Image Pro Plus 5.1 by Media Cybernetics.

Results

Figure 18:
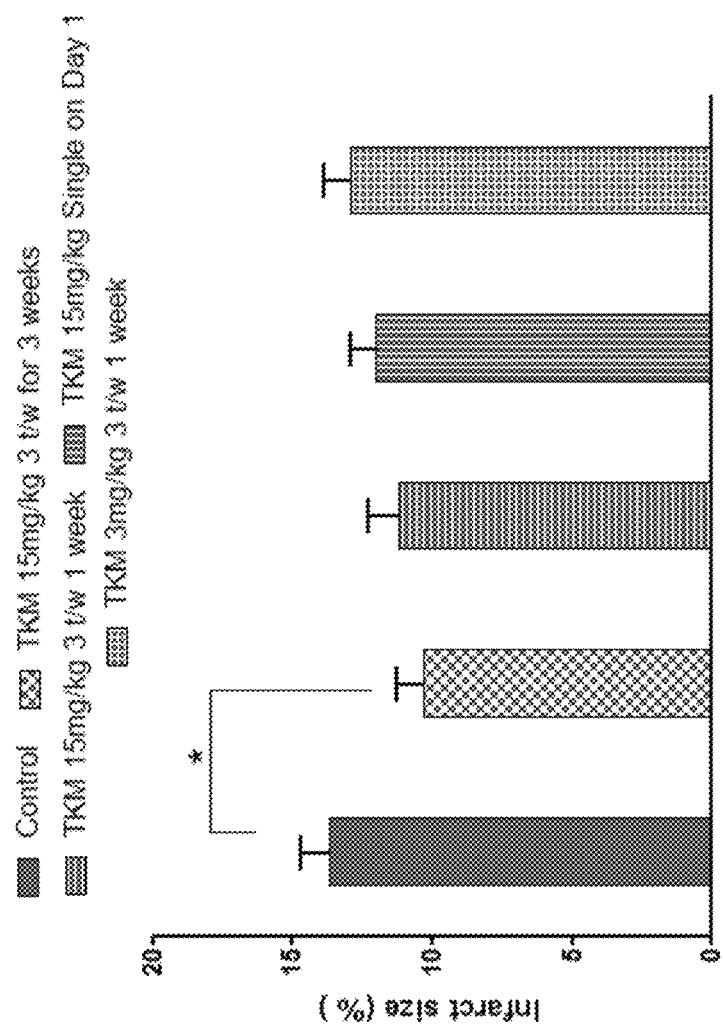
FIG. 18 illustrates the infarct size 35 days after MI induction.

FIG. 18 illustrates the infarct size 35 days after MI induction. All treatment groups had smaller average infarct size as compared to the untreated control group. There was a significant difference between the treatment group 2M and the control group 1M.

Figure 19:
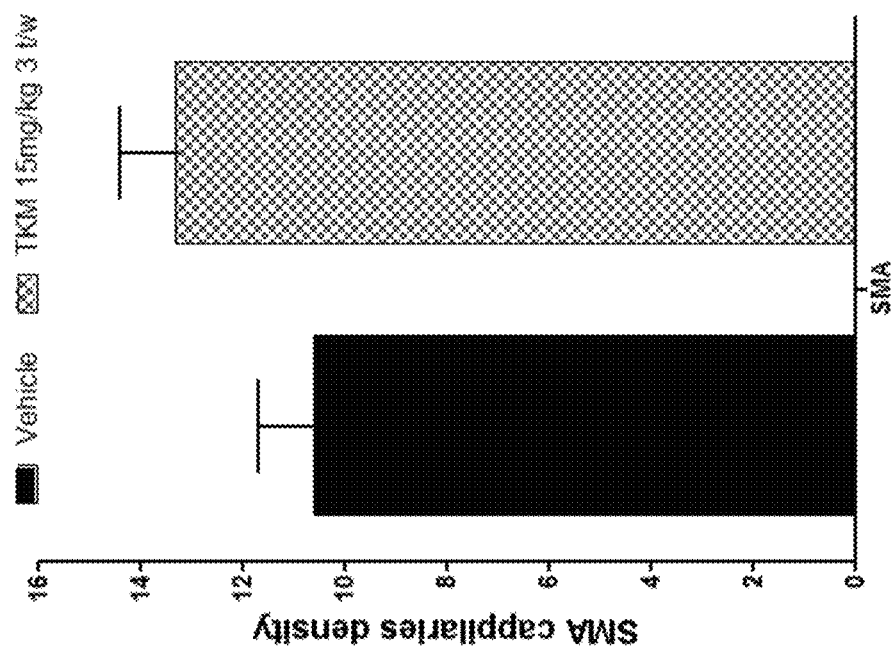
FIG. 19 compares SMA staining 35 days after MI induction for dextran sulfate treatment (15 mg/kg 3 times/week for 3 weeks) and vehicle control group.

FIG. 19 compares SMA staining 35 days after MI induction for treatment group 2M and control group 1M. Dextran sulfate treatment resulted in a higher SMA capillary density as compared to vehicle control.

Figure 20B:
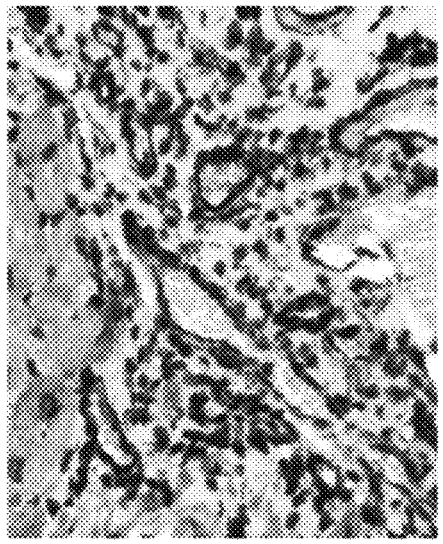
FIGS. 20A-20C illustrate SMA staining for vascular density for two dextran sulfate treated (15 mg/kg 3 times/week for 3 weeks) rats (FIGS. 20A, 20B) and one vehicle control rat (FIG. 20C).
Figure 20C:
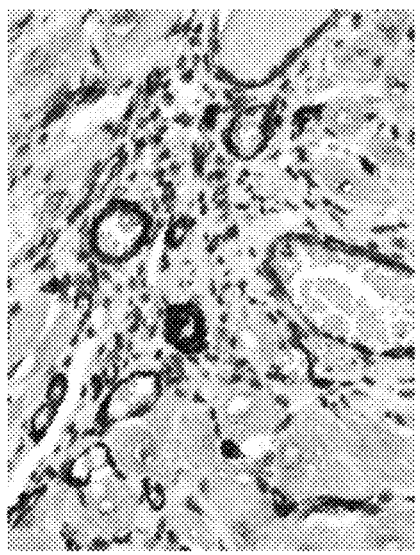
Figure 20A:
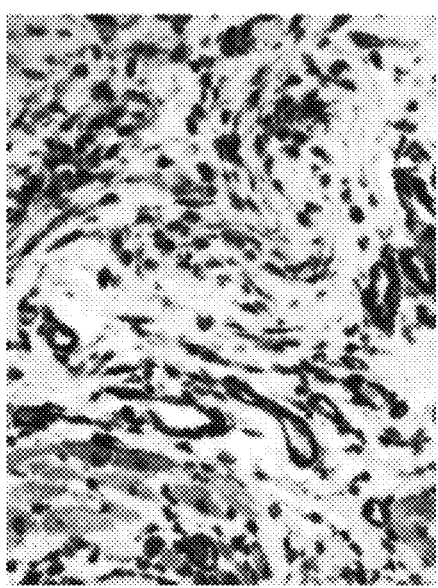

FIGS. 20A-20C illustrate pictures of SMA staining for vascular density for two rats in the 2M treatment group (FIGS. 20A and 20B) and one rat in the 1M control group (FIG. 20C). Dextran sulfate treatment resulted in higher SMA vascular density as compared to vehicle control.

Dextran sulfate significantly decreased the infarct volume in the treated group 2M following myocardial infarction in rats as compared to the control vehicle treated group. The same dextran sulfate treated group revealed a trend of increase in capillaries density in the infarct region of the hearts compared to the control vehicle treated group. Dextran sulfate thereby promotes myocardial and blood vessels repair and enhance angiogenesis in the infarct region following myocardial infarction. This may improve the long-term left ventricular remodeling, and enhance the recovery of the left ventricular function.

Example 4

Evaluation of Angiogenesis Efficacy in Rat Hind-Limb Ischemia Model

In the study described above in Example 1 the angiogenic efficacy of dextran sulfate was proven in a stable severe ischemia model in mice. In this study a stable severe ischemia model in rats (Toakai *J Exp Clin Med* 31(3), 128-13 (2006)) was applied to assess efficacy of dextran sulfate on angiogenesis and functional outcome by using the different animal's species.

Materials

Dextran sulfate solutions were prepared the day before initiation of the study. As vehicle, 0.9% NaCl (saline) was used. The relevant volume of NaCl was added to the weighed compound to obtain the concentration of 6 and 60 mg/ml, which corresponds to administration of 0.5 ml/kg to obtain the dose of 3 and 30 mg/kg respectively. Dextran sulfate (average molecular weight within a range of 5-7 kDa was obtained from pK Chemicals A/S, Denmark) was dissolved by vortexing or simply by turning the tube a few times. The solution was stored at 4° C. overnight for aggregates to stabilize. The next day, the tube was vortexed and filtered through a 0.2 µm filter to obtain a sterile solution. The preparation was considered reliable for up to 15 days when stored at 4° C. Solutions were prepared on Day 7 and used on Days 8-21; a second preparation was made on Day 21, and used on Days 22-28.

90 made SD rate with an average body weight of 277 g at study initiation (Day 0) were obtained from Harlan Laboratories, Israel. Animals were fed ad libitum a commercial rodent diet (Teklad Certified Global 18% Protein Diet). Animals had free access to acidified drinking water (pH between 2.5 and 3.5).

Animals were handled according to guidelines of the National Institute of Health (NIH) and the Association for Assessment and Accreditation of Laboratory Animal Care (AAALAC). Animals were housed in polyethylene cages (3/cage) measuring 35×30×15 cm, with stainless steel top grill facilitating pelleted food and drinking water in plastic bottle; bedding: steam sterilized clean paddy husk (Harlan, Sani-chip cat #: 7090A) were used and bedding material was changed along with the cage at least twice a week. Animals were fed ad libitum a commercial rodent diet (Teklad Certified Global 18% Protein Diet cat #: 106S8216). Animals had free access to autoclaved and acidified drinking water (pH between 2.5 and 3.5) obtained from the municipality supply. Animals were housed under standard laboratory conditions, air-conditioned and filtered (HEPA F6/6) with adequate fresh air supply (Minimum 15 air changes/hour). Animals were kept in a climate-controlled environment. Temperatures range was 20-24° C. and relative humidity (RH) range was 30-70% with 12 hours light and 12 hours dark cycle.

All surgical procedures were performed under anesthesia and analgesia (1.5 to 3.0% isoflurane, 1.5% $N_2O$ and 0.5% $O_2$). A 0.5-1.0 cm incision was made in the skin in the inguinal area. The femoral artery and vein were ligated twice with 4-0 silk thread and transected between the ligatures. The wound was closed with 3-0 silk thread and the rats were allowed to recover.

On Day 8, Week 2 post-surgery, each animal in groups 1M, 2M, and 3M was injected s.c. three times a week. Animals in group 4M and 5M were injected s.c. once on Day 8, see Table 12.

TABLE 12

Group allocation

| Group | Treatment | Volume | Administration route |
|---|---|---|---|
| 1M (n = 17) | Vehicle control | 0.5 ml/kg | s.c. repeated 3 times a week, starting on Day 8 |
| 2M (n = 18) | Dextran sulfate, 30 mg/kg | | |
| 3M (n = 17) | Dextran sulfate, 30 mg/kg | | |
| 4M (n = 17) | Dextran sulfate, 30 mg/kg | | s.c. administered once on Day 9 |
| 5M (n = 17) | Dextran sulfate, 3 mg/kg | | |

Blood Flow Measurement

Blood flows in legs from both sides were measured with a non-contact LASER Doppler before surgery on Day −1 and on Days: 1, 7, 14, 21 and 28 post operation. Blood flow measurements were expressed as the ratio of the flow in the ischemic limb to that in the normal limb.

Figure 21:
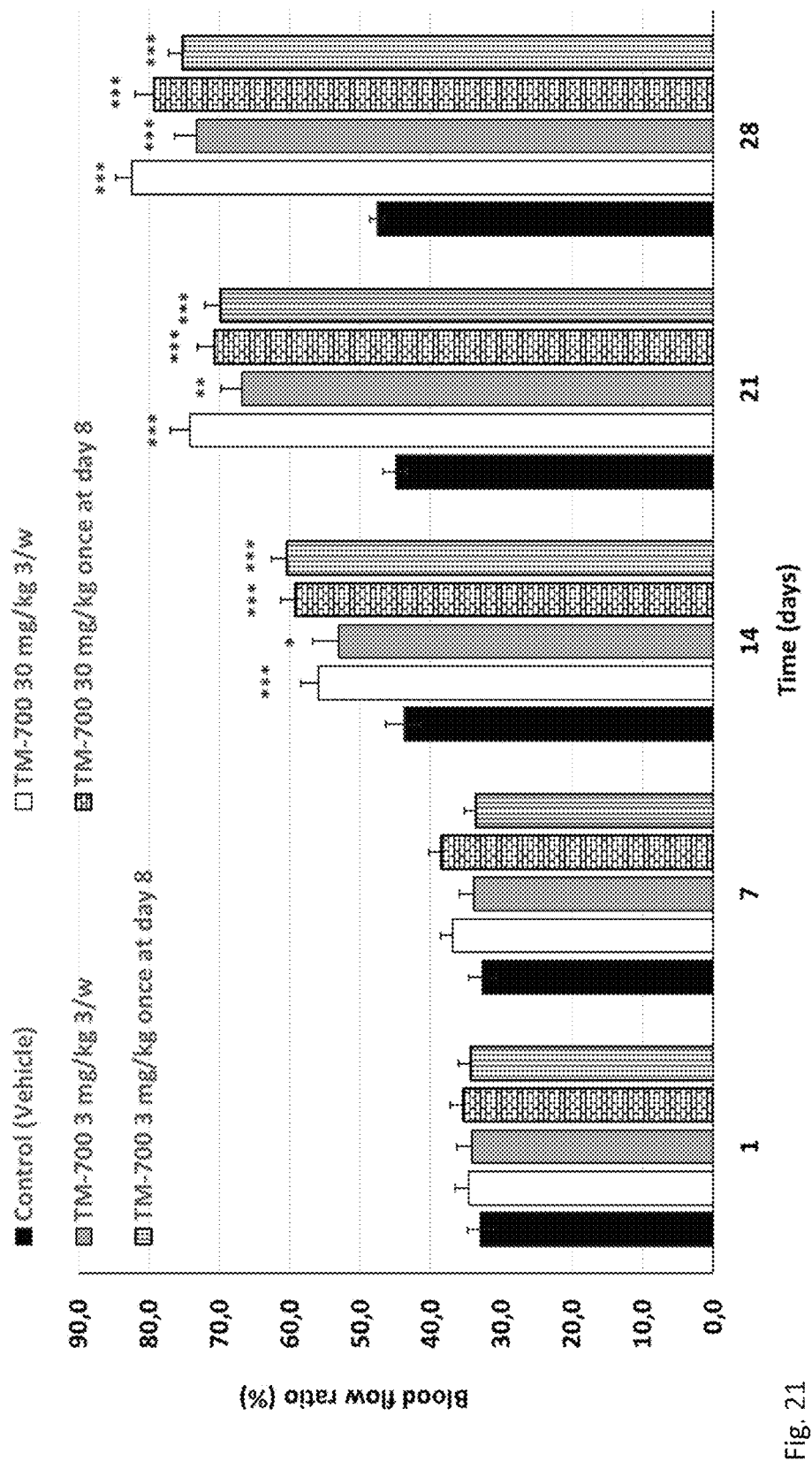
FIG. 21 illustrates mean blood flow in a rat HLI model.

All treated animal groups exhibited marked increase of blood flow in the operated limb compare to the vehicle treated control between Day 1 and Day 28, see Table 13 and FIG. 21. There were statistically significant differences between all group treated with dextran sulfate compared to the vehicle treated control.

TABLE 13

Mean change in blood flow

| Group | Mean change in blood flow from Day 0 to Day 28 (%) |
|---|---|
| 1M | 14.8 |
| 2M | 47.7 |
| 3M | 39.1 |
| 4M | 44.0 |
| 5M | 41.0 |

FIG. 21 shows the ratio of blood flow between the HLI-injured versus non-injured leg measured by a non-contact LASER doppler. The different groups were compared using two-way ANOVA for repeated measures, followed by Bonferroni post-hoc test. Comparison of dextran sulfate treated group 2M, 3M, 4M and 5M to control group 1M revealed statistically significant differences from Day 14 through Day 28 (*$P<0.05$;$P<0.01$;*$P<0.001$).

Ischemic Severity

The ischemic limb was macroscopically evaluated weekly from Day 7 up to Day 28 by using graded morphological scales for necrotic area (see Table 4). In all animal groups treated with dextran sulfate and vehicle no toe necrosis or foot amputation was found.

In Vivo Assessment of Limb Function and Ischemic Damage

Semi-quantitative assessment of impaired use of the ischemic limb was performed once a week post-surgery using the scale presented in Table 7. Scoring was performed by personnel blinded to the treatment.

Figure 22:
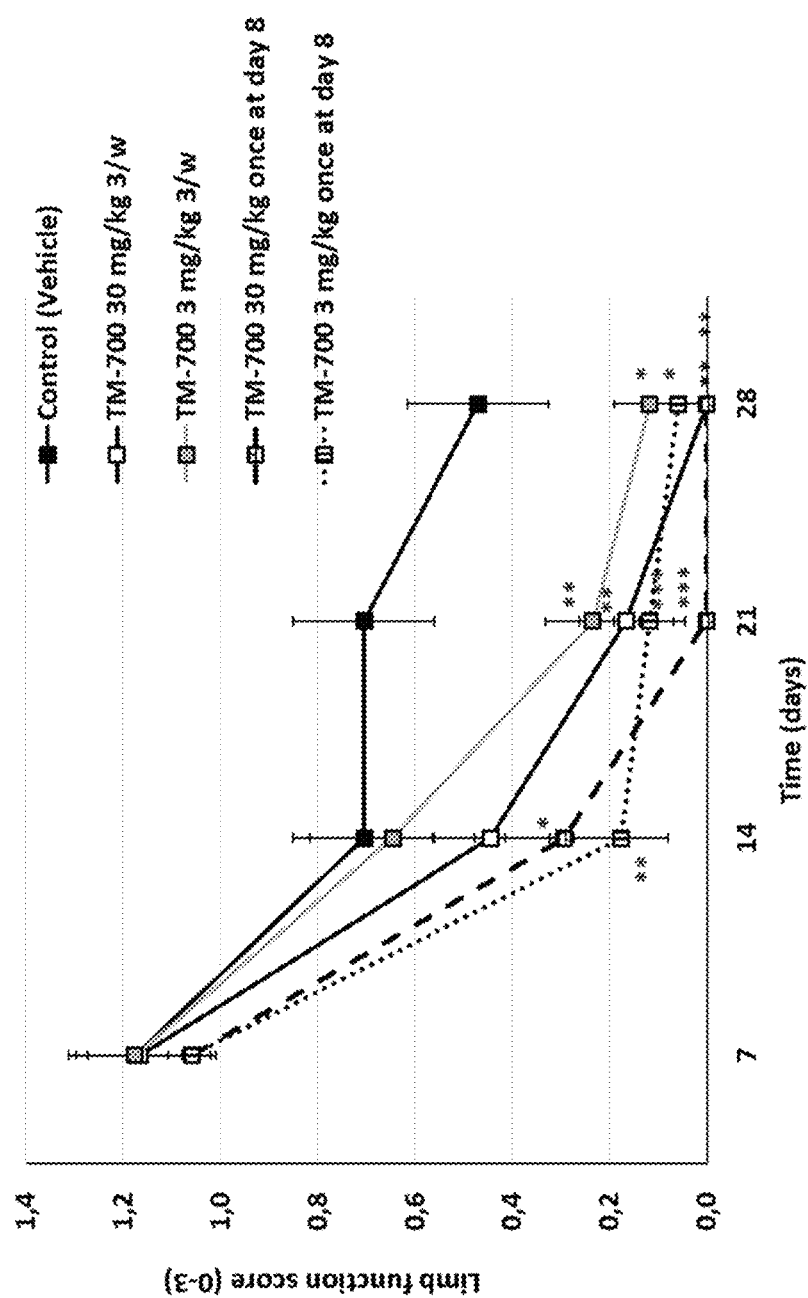
FIG. 22 illustrates limb scores in a rat HLI model.

All animal groups treated with dextran sulfate had limb functional improvement compared to the vehicle treated control between Day 1 and Day 28, see Table 14 and FIG. 22.

TABLE 14

Incidence of rats with limb function scores 0-3 on Day 28

| Group | Incidence of limb function score 0 (%) | Incidence of limb function score 1 (%) | Incidence of limb function score 2 (%) | Incidence of limb function score 3 (%) |
|---|---|---|---|---|
| 1M | 59 | 35 | 6 | 0 |
| 2M | 100 | 0 | 0 | 0 |
| 3M | 88 | 12 | 0 | 0 |
| 4M | 100 | 0 | 0 | 0 |
| 5M | 94 | 6 | 0 | 0 |

The different groups were compared using two-way ANOVA for repeated measures, followed by Bonferroni post-hoc test. Comparison of dextran sulfate treated group 2M, 3M, 4M and 5M to control group 1M revealed statistically significant differences from Day 14 through Day 28 (*$P<0.05$;$P<0.01$;*$P<0.001$).

Immunohistochemistry and Analysis of Capillaries Density

Figure 23:
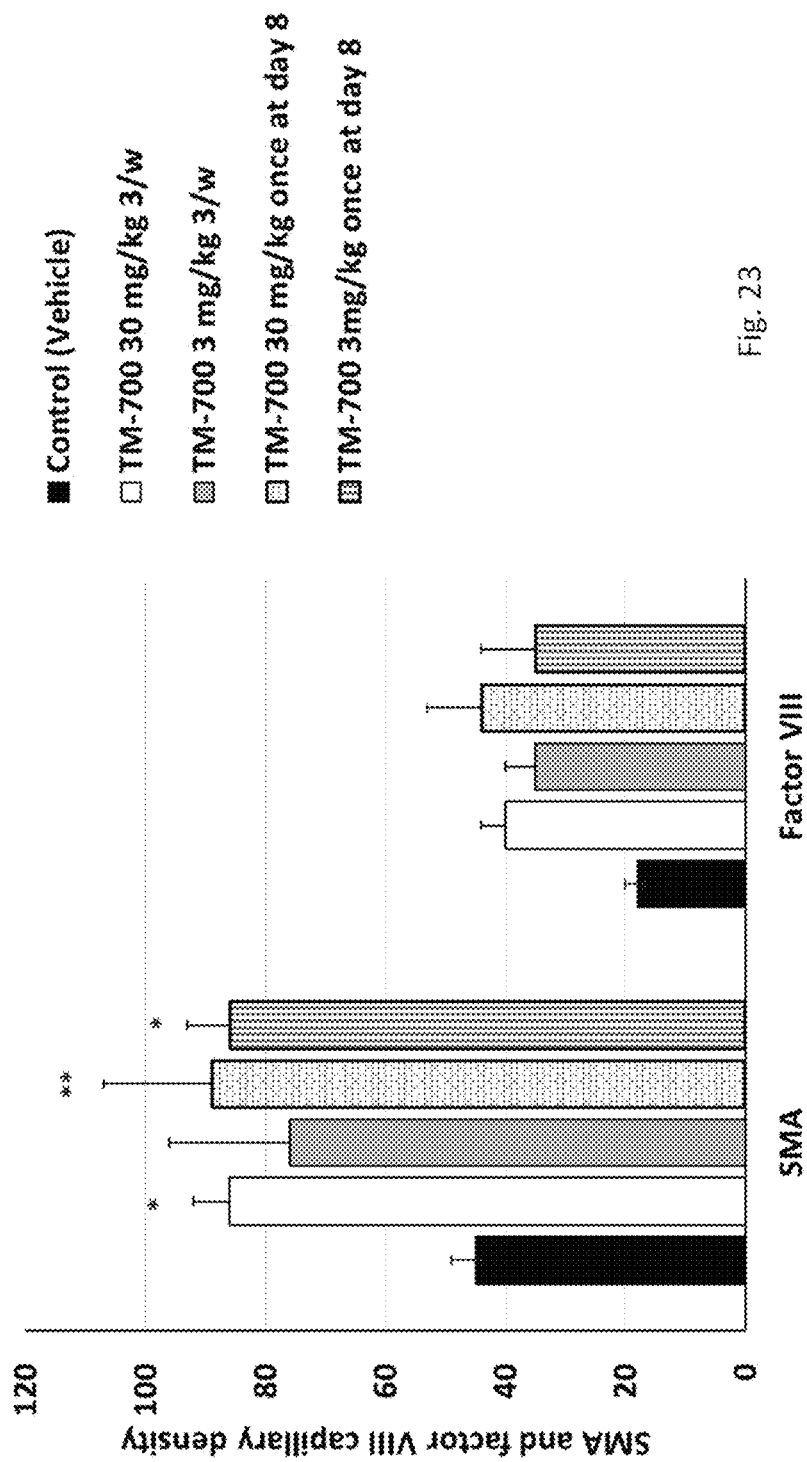
FIG. 23 illustrates SMA and factor 8 capillary density in HLI-injured leg.
Figure 24:
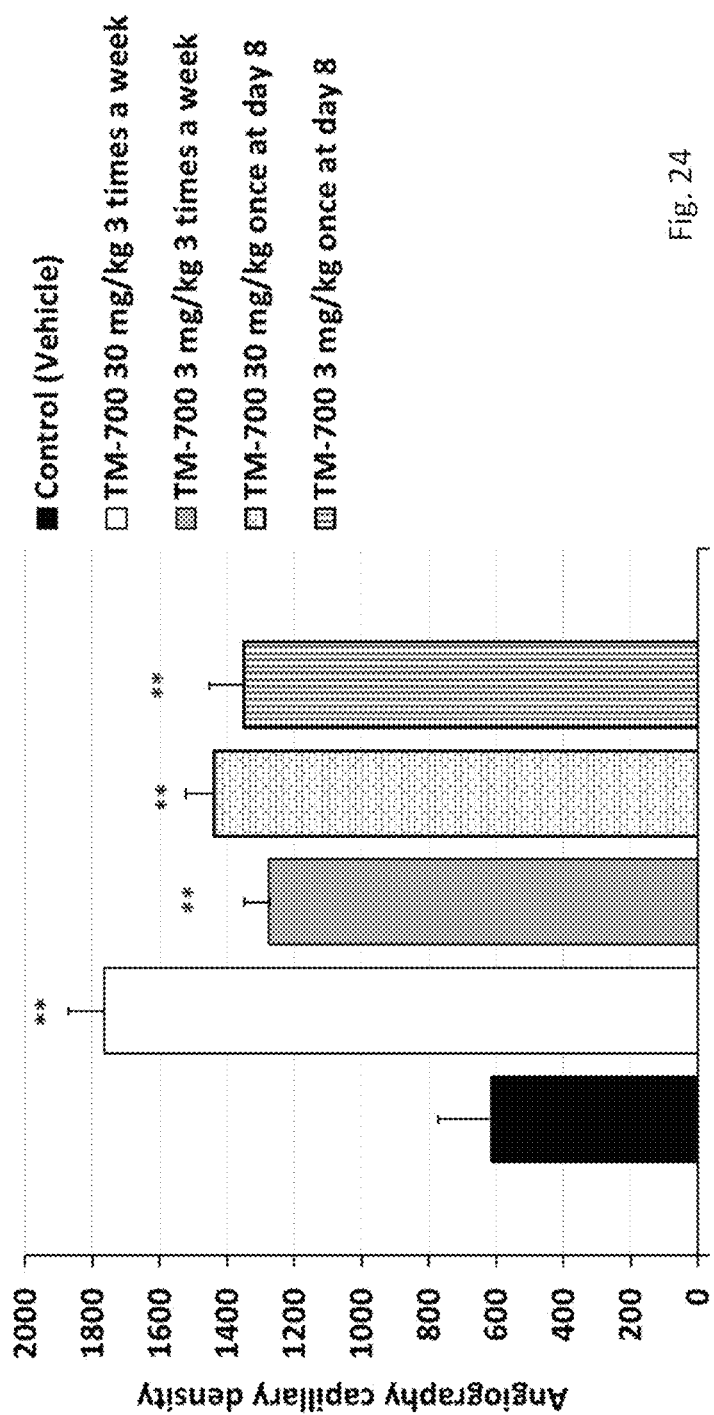
FIG. 24 illustrates angiography capillaries score in HLI-injured leg.
Figures 25A, 25B, 25C, 25D:
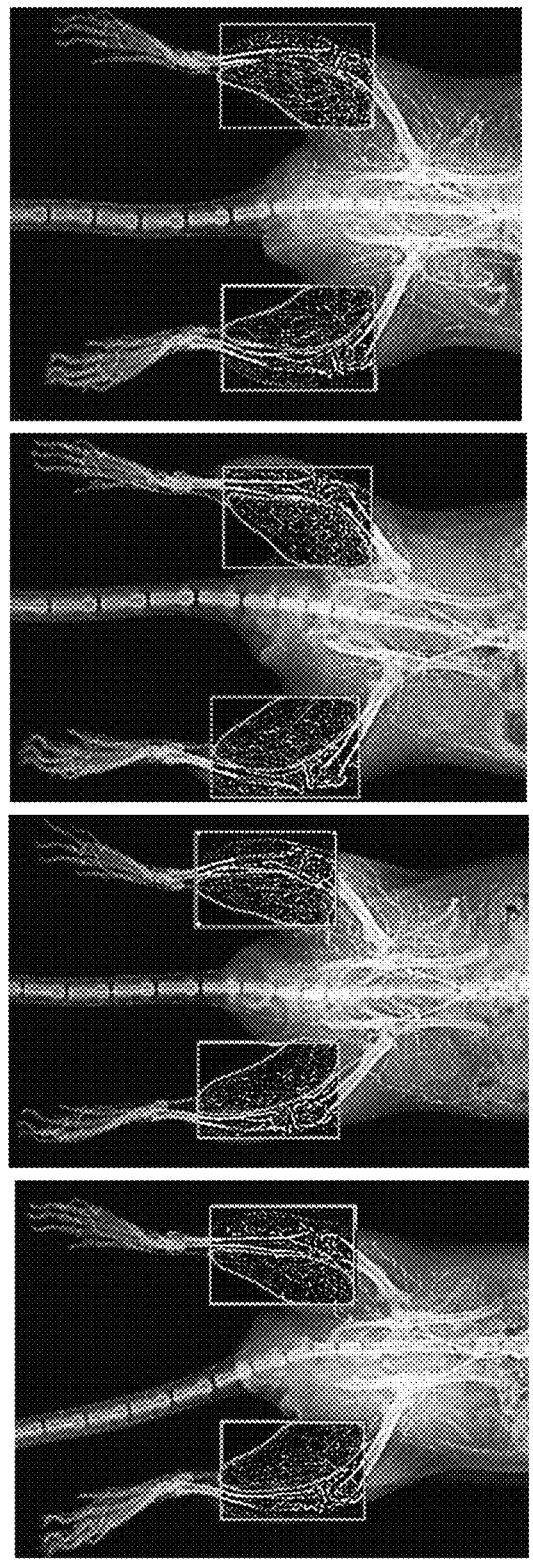
FIGS. 25A-25D illustrate angiography capillaries images of vehicle control animal (FIG. 25A) and animals in treatment groups 2M, 3M and 4M (FIGS. 25B-25D).

Four sections of muscle samples were taken from the same areas of six animals from groups 1M, 2M, 3M, 4M, 5M and stained for blood vessels using antibodies against SMA and Factor 8. The area of blood vessels was evaluated by using image analysis. Density was expressed as the mean number of capillaries per field of view. Total vessels represented all blood vessels in the measured area. The number of SMA and factor 8 positive capillaries in right ischemic limb was larger in all dextran sulfate treated groups 2M-5M compared to the control group 1M on Day 28 of the study, see FIG. 23. SMA and factor 8 positive staining are considered as an indication for small capillaries formation in rats, and thus the obtained results supported blood flow improvement observed in the animal groups treated with dextran sulfate. Statistical analysis performed using two-way ANOVA followed by Bonferroni multiple comparisons, */** indicate p<0.0510.01.

Angiography Analysis

The number of intersections between contrast-filled vessels was determined by image analysis 28 days after induction of hind-limb ischemia. The angiography revealed significantly large numbers of collaterals in affected limb in rats treated with dextran sulfate compare to the vehicle treated control group (p<0.01 and p<0.001 according to one-way ANOVA followed by Bonferroni post-hoc test), see FIGS. 24 and 25A-25D.

Impaired angiogenesis is one of the features of ischemic diseases. The most established target for therapeutic angiogenesis has been VEGF and its receptors. However, clinical trials to alleviate ischemia were disappointing, indicating the need for new therapeutic targets to treat ischemic diseases.

In the present study blood flow improvement in the rat hind-limb ischemia model was examined in order to evaluate the efficacy of dextran sulfate in two different doses and treatment regimes. Dextran sulfate administration at a doses of 30 and 3 mg/kg s.c. three times a week or in single dose on Day 8 restored significantly blood perfusion and improved limb functional score compared to the vehicle treated control from Day 14 after surgery. Both doses and administration regimens were efficacious. No spontaneous amputations or toe necrosis occurred in any of the treated or control animal groups. Dextran sulfate treatment did not cause any adverse effects in the treated animals. The angiography score (measure of collateral artery enlargement) was significantly greater in all animal groups treated with dextran sulfate compared to the vehicle treated groups, with no statistical difference between the various treated groups. SMA and factor 8 capillaries density also increased after dextran sulfate treatment. Collectively the data of this study confirmed the therapeutic efficacy of dextran sulfate for the treatment of occlusive peripheral arterial disease in the rat hind-limb ischemia model.

The embodiments described above are to be understood as a few illustrative examples of the present invention. It will be understood by those skilled in the art that various modifications, combinations and changes may be made to the embodiments without departing from the scope of the present invention. In particular, different part solutions in the different embodiments can be combined in other configurations, where technically possible. The scope of the present invention is, however, defined by the appended claims.

The invention claimed is:

1. A method for selectively inducing angiogenesis in an ischemic tissue or organ of a human subject suffering from a disease, disorder or medical condition causing the ischemia in a tissue or organ in the human subject, the method comprising selectively inducing angiogenesis in the ischemic tissue or organ of the human subject while not causing any significant blood vessel formation in non-ischemic tissue of the human subject by intravenously or subcutaneously administering dextran sulfate, or a pharmaceutically acceptable salt thereof, having an average molecular weight below 10 000 Da to the human subject for selectively inducing angiogenesis in the an ischemic tissue or organ of the human subject while not causing any significant blood vessel formation in non-ischemic tissue of the human subject, wherein the disease, disorder or medical condition is selected from a group consisting of wound healing, peripheral ischemia, ischemia following transplantation of organ, tissue and/or cells, peripheral arterial disease, limb ischemia, restless leg, Raynaud's syndrome, sickle cell disease, thromboangiitis obliterans, coronary ischemia, congestive heart failure, myocardial infarction, a coronary arterial disease, an ischemic disease in children, a perinatal or neonatal disease, neonatal hypoxic brain injury, neonatal ischemic brain injury, asphyxia encephalopathy, cerebral palsy, ischemia in central nervous system, traumatic brain injury, temporal arteritis, hypoxia caused by multiple sclerosis, stroke, amyotrophic lateral sclerosis, muscular dystrophic diseases, ischemia caused by thrombotic, hemorrhagic or traumatic injuries.

2. The method according to claim to 1, wherein the average molecular weight is within a range of 2 000 and 10 000 Da.

3. The method according to claim 2, wherein the average molecular weight is within a range of 3 000 and 10 000 Da.

4. The method according to claim 3, wherein the average molecular weight is within a range of 3 500 and 9 500 Da.

5. The method according to claim 4, wherein the average molecular weight is within a range of 4 500 and 7 500 Da.

6. The method according to claim 5, wherein the average molecular weight is within a range of 4 500 and 5 500 Da.

7. The method according to claim 1, wherein the dextran sulfate, or said pharmaceutically acceptable salt thereof, has an average sulfur content in a range from 15 to 20%.

8. The method according to claim 7, wherein the average sulfur content is about 17%.

9. The method according to claim 1, wherein the dextran sulfate, or the pharmaceutically acceptable salt thereof, has a number average molecular weight ($M_n$) as measured by nuclear magnetic resonance (NMR) spectroscopy within an interval of 1850 and 2000 Da.

10. The method according to claim 9, wherein the dextran sulfate, or the pharmaceutically acceptable salt thereof, has on average 5.1 glucose units and an average sulfate number per glucose unit of 2.6 to 2.7.

11. The method according to claim 1, wherein the dextran sulfate, or the pharmaceutically acceptable salt thereof, is formulated as an aqueous injection solution.

12. The method according to claim 1, wherein the dextran sulfate, or the pharmaceutically acceptable derivative thereof, is formulated to be intravenously or subcutaneously administered at a dosage in a range from 0.05 to 50 mg/kg of body weight of the human subject.

13. The method according to claim 12, wherein the dextran sulfate, or the pharmaceutically acceptable derivative thereof, is formulated to be intravenously or subcutaneously administered at a dosage in a range from 0.05 to 30 mg/kg of body weight of the human subject.

14. The method according to claim 13, wherein the dextran sulfate, or the pharmaceutically acceptable derivative thereof, is formulated to be intravenously or subcutaneously administered at a dosage in a range from 0.1 to 15 mg/kg body weight of the human subject.

15. The method according to claim 14, wherein the dextran sulfate, or the pharmaceutically acceptable derivative thereof, is formulated to be intravenously or subcutaneously administered at a dosage in a range from 0.1 to 10 mg/kg body weight of the human subject.

16. The method according to claim 1, wherein said pharmaceutically acceptable salt thereof is a sodium salt of dextran sulfate.

* * * * *